(12) United States Patent
Ishikawa et al.

(10) Patent No.: US 8,309,057 B2
(45) Date of Patent: Nov. 13, 2012

(54) METHODS FOR ELEVATING NEUROTROPHIC AGENTS

(75) Inventors: Muriel Y. Ishikawa, Livermore, CA (US); Edward K. Y. Jung, Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 553 days.

(21) Appl. No.: 11/150,861

(22) Filed: Jun. 10, 2005

(65) Prior Publication Data

US 2006/0282062 A1  Dec. 14, 2006

(51) Int. Cl.
*A61K 49/00* (2006.01)
*A61K 35/30* (2006.01)
*A61K 9/00* (2006.01)

(52) U.S. Cl. .................... 424/9.2; 424/570; 424/400

(58) Field of Classification Search .................. None
See application file for complete search history.

(56) References Cited

U.S. PATENT DOCUMENTS

| | | |
|---|---|---|
| 5,476,446 A | 12/1995 | Arenburg |
| 5,641,750 A | 6/1997 | Louis |
| 5,676,655 A | 10/1997 | Howard, III et al. |
| 5,713,847 A | 2/1998 | Howard, III et al. |
| 5,797,898 A | 8/1998 | Santini, Jr. et al. |
| 5,929,041 A | 7/1999 | Magal |
| 6,043,221 A | 3/2000 | Magal et al. |
| 6,045,528 A | 4/2000 | Arenberg et al. |
| 6,075,066 A | 6/2000 | Matsuda et al. |
| 6,201,980 B1 | 3/2001 | Darrow et al. |
| 6,225,282 B1 | 5/2001 | Gao |
| 6,278,379 B1 | 8/2001 | Allen et al. |
| 6,291,510 B1 | 9/2001 | Hamilton et al. |
| 6,291,516 B1 | 9/2001 | Dudek et al. |
| 6,304,787 B1 | 10/2001 | Kuzma et al. |
| 6,309,410 B1 | 10/2001 | Kuzma et al. |
| 6,310,040 B1 | 10/2001 | Bozyczko-Coyne et al. |
| 6,331,523 B1 | 12/2001 | Kljavin et al. |
| 6,408,878 B2 | 6/2002 | Unger et al. |
| 6,429,191 B1 | 8/2002 | Gao |
| 6,432,050 B1 | 8/2002 | Porat et al. |
| 6,440,102 B1 | 8/2002 | Arenberg et al. |
| 6,453,195 B1 | 9/2002 | Thompson |
| 6,454,759 B2 | 9/2002 | Krulevitch et al. |
| 6,464,687 B1 | 10/2002 | Ishikawa et al. |
| 6,480,730 B2 | 11/2002 | Darrow et al. |
| 6,537,256 B2 | 3/2003 | Santini, Jr. et al. |
| 6,551,838 B2 | 4/2003 | Santini, Jr. et al. |
| 6,586,023 B1 | 7/2003 | Song et al. |
| 6,668,190 B2 | 12/2003 | Iezzi et al. |
| 6,669,683 B2 | 12/2003 | Santini, Jr. et al. |
| 6,673,596 B1 | 1/2004 | Sayler et al. |
| 6,684,879 B1 | 2/2004 | Coffee et al. |
| 6,723,077 B2 | 4/2004 | Pickup et al. |
| 6,726,678 B1 | 4/2004 | Nelson et al. |
| RE38,525 E | 6/2004 | Stanley et al. |
| 6,750,311 B1 | 6/2004 | Van Antwerp et al. |
| 6,751,491 B2 | 6/2004 | Lew et al. |
| 6,754,536 B2 | 6/2004 | Swoyer et al. |
| 6,756,053 B2 | 6/2004 | Zhang et al. |
| 6,758,810 B2 | 7/2004 | Lebel et al. |
| 6,770,179 B1 | 8/2004 | Nanci |
| 6,855,690 B2 | 2/2005 | Benowitz et al. |
| 2003/0032892 A1 | 2/2003 | Erlach et al. |
| 2003/0158584 A1 | 8/2003 | Cates et al. |
| 2003/0181461 A1 * | 9/2003 | Lautt et al. ............... 514/252.16 |
| 2003/0220280 A1 * | 11/2003 | Bunge et al. .................... 514/44 |
| 2003/0224735 A1 | 12/2003 | Moursund et al. |
| 2004/0127942 A1 | 7/2004 | Yomtov et al. |
| 2004/0140209 A1 | 7/2004 | Choi et al. |

FOREIGN PATENT DOCUMENTS

| | | |
|---|---|---|
| CN | 1561241 A | 1/2005 |
| WO | WO 98/49308 | 11/1998 |
| WO | WO 02/45749 A2 | 6/2002 |
| WO | WO 02/089767 A1 | 11/2002 |
| WO | WO 03/065994 A2 | 8/2003 |
| WO | WO 03/082380 A1 | 10/2003 |

OTHER PUBLICATIONS

Gong et al., J. Clin Invest. 114: 1624-1634, 2004.*
Poduslo et al. J Neurochem. 65: 149-159, 1995.*
Perry & Higgs, Curr Opin in Chem Biol. 2: 472-481, 1998.*
Saragovi et al., Tips 21: 93-98, 2000.*
Wu, J Amer Soc for Expt NeuroTherapeutics 2: 120128, 2005.*
Barad et al., PNAS 95: 15020-15025, 1998.*
Sommer et al., J Neuroimmunol. 79: 54-61, 1997.*
Walikonis et al Jour Biol Chem. 273: 9070-9077, 1998.*
Zou et al., Neuropharmacology 39: 324-333, 2000.*
Pearse et al., Nature Med 10: 610-616, 2004.*
Souness et al., Immunopharmacology 47: 127-162, 2000.*
Lu et al. Eur J. Neurosc 19: 2669-2681, 2004.*
Vendetti et al. J Leukoc Biol. 80: 880-888, 2006.*
MacNeal RJ, Structure and Function: Biology of the Skin: Merck Manual Home Edition, 2006.*
Gupta J Postgrad Med 48: 218-225, 2002—online article (retrieved on Jan. 2, 2010).*
Adler, Ruben; Curcio, Christine; Hicks, David; Price, Donald, and Wong, Fulton; "Cell Death in Age-Related Macular Degeneration"; bearing dates of May 24, 1999, Nov. 2, 1999 and Nov. 3, 1999; pp. 31-36; vol. 5; located at http://www.molvis.org/molvis/v5/p31; Molecular Vision; printed on Mar. 9, 2005.
Bawa, Rajan; Siegel, Ronald A.; Marasca, Brian; Karel, Marcus; and Langer, Robert; "An Explanation for the Controlled Release of Macromolecules From Polymers"; Journal of Controlled Release; 1985; pp. 259-267; vol. 1; Elsevier Science Publishers B.V., Amsterdam-Printed in Netherlands.

(Continued)

*Primary Examiner* — Daniel E Kolker
*Assistant Examiner* — Aditi Dutt
(74) *Attorney, Agent, or Firm* — Workman Nydegger

(57) ABSTRACT

Methods and systems are described that release one or both of a neurotrophin and an inhibitor of the degradation of the neurotrophin within or in the vicinity of a highly innervated tissue. In some embodiments, the method includes regulating the release of the neurotrophin and the inhibitor of degradation over time. In some embodiments, the method includes monitoring the concentration of the neurotrophin over time. The system may include a device or multiple devices for the release of the neurotrophin and the inhibitor as well as a controller. In some embodiments the system may include a sensor device and/or an imaging device capable of detecting the concentration of the neurotrophin over time. The release of the neurotrophin and inhibitor of degradation may be part of a controlled release system and regulated over time.

43 Claims, 5 Drawing Sheets

OTHER PUBLICATIONS

Brannon-Peppas, Lisa; "Biomaterials: Polymers in Controlled Drug Delivery"; Medical Plastics and Biomaterials Magazine; bearing dates of Nov. 1997 and 2001; pp. 1-16; located at: http://www.devicelink.com/mpb/archive/97/11/003.html; Cannon Communications LLC; printed on Mar. 18, 2005.

Brown, L. R.; Wei, C. L.; and Langer, R.; "In Vivo and In Vitro Release of Macromolecules from Polymeric Drug Delivery Systems"; Journal of Pharmaceutical Sciences; Oct. 1983; pp. 1181-1185; vol. 72, No. 10; American Pharmaceutical Association.

Cai, Dongming; Qiu, Jin; Cao, Zixuan; McAtee, Marietta; Bregman, Barbara S.; and Filbin, Marie T.; "Neuronal Cyclic AMP Controls the Developmental Loss in Ability of Axons to Regenerate."; The Journal of Neuroscience; Jul. 1, 2001; pp. 4731-4739; vol. 21, No. 13; Society for Neuroscience; located at: http://www.jneurosci.org/cgi/content/full/21/13/4731?maxtoshow=&HITS=10&hits=10&RESULTFORMAT=&fulltext=Neuronal+Cyclic+AMP+Controls+the+Developmental+Loss+in+Ability+of+Axons+to+Regenerate&searchid=1118333884773_5929&stored=search=&FIRSTINDEX=0&volume=21&issue=13&journalcode=jneuro; printed on Mar. 22, 2005.

Castrén, Eero; "Neurotrophins as Mediators of Drug Effects on Mood, Addiction, and Neuroprotection"; Molecular Neurobiology; 2004; pp. 289-301; vol. 29; Humana Press Inc.

Castrén, Eero; "Neurotrophic Effects of Antidepressant Drugs"; Current Opinion in Pharmacology; bearing dates of 2003 and 2004; pp. 58-64; vol. 4; Elsener Ltd.; located at : www.sciencedirect.com.

Chao, Moses V.; "Neurotrophins and Their Receptors: A Convergence Point for Many Signalling Pathways"; Nature Reviews/Neuroscience; Apr. 2003; pp. 299-309; vol. 4; Nature Publishing Group; printed on Mar. 9, 2005.

Ciulla, Thomas A., M.D.; Amador, Armando G., M.D.; Zinman, Bernard, MDCM, FRCP(C), FACP; "Diabetic Retinopathy and Diabetic Macular Edema: Pathophysiology,Screening, and Novel Therapies"; Diabetes Care, bearing a date of Sep. 2003, pp. 2653-2664, vol. 26, No. 9; American Diabetes Association.

D'Sa, Carrol; Duman, Ronald S.; "Antidepressants and Neuroplasticity"; Bipolar Disorders; 2002; pp. 183-194; vol. 4; Blackwell Munksgaard.

"Efficacy & Safety Studies for Reversing Deafness Using Trophic Factors"; The Bionic Ear Institute—Research; bearing dates of Feb. 19, 2004 and Jun. 24, 2004; p. 1; located at: http://www.bionicear.org/bei/ResEfficacySafety.html; printed on Mar. 17, 2005.

Goodell, John A.; Flick, Arthur B.; Hebert, James C.;and Howe, James G.; "Preparation and Release Characteristics of Tobramycin-Impregnated Polymethylmethacrylate Beads"; American Journal of Hospital Pharmacy; Jun. 1986; pp. 1454-1461; vol. 43; American Society of Hospital Pharmacists, Inc.

Green, W. Richard; "Histopathology of Age-Related Macular Degeneration"; bearing dates of May 24, 1999, Nov. 2, 1999, and Nov. 3, 1999; pp. 27-36; vol. 5; located at http://www.molvis.org/molvis/v5/p27; Molecular Vision; printed on Mar. 9, 2005.

Grill, Warren M. PhD; McDonald, John W. PhD; Peckham, P. Hunter PhD; Heetderks, William MD, PhD; Kocsis, Jeffery PhD; and Weinrich, Michael MD; "At the Interface: Convergence of Neural Regeneration and Neural Prostheses for Restoration of Function"; Journal of Rehabilitation Research and Development; bearing dates of Nov. 2001 and Dec. 2001; pp. 1-7; vol. 38, No. 6; located at: http://www.vard.org/jour/01/38/6/mcdon386.htm; printed on Mar. 17, 2005.

Heeger, David J. and Ress, David; "What Does fMRI Tell Us About Neuronal Activity?"; Nature Reviews/Neuroscience; Feb. 2002; pp. 142-151; vol. 3; MacMillan Magazines Ltd.; printed on Mar. 9, 2005.

Hefti, Franz; "Pharmacology of Neurotrophic Factors"; Annu. Rev. Pharmacol. Toxicol.; 1997; pp. 239-267; vol. 37; Annual Reviews, Inc.; printed on Mar. 9, 2005.

Hjelmeland, Leonard M.; Cristofalo, Vincent J.; Funk, Walter; Rakoczy, Elizabeth; and Katz, Martin L.; "Senescence of the Retinal Pigment Epithelium"; bearing dates of May 24, 1999, Nov. 2, 1999 and Nov. 3, 1999; pp. 33-36; vol. 5; Molecular Vision; printed on Mar. 9, 2005.

Hochhaus, Frederike; Koehne, Petra; Schäper, Christoph; Butenandt, Otfrid; Felderhoff-Mueser, Ursula; Ring-Mrozik, Elfride; Obladen, Michael; and Bührer, Christoph; "Elevated Nerve Growth Factor and Neurotrophin-3 Levels in Cerebrospinal Fluid of Children With Hydrocephalus"; bearing dates of Aug. 24, 2001, May 21, 2001, and Aug. 24, 2001; Biomed Central, BMC Pediatrics 2001; pp. 1-8; vol. 1, Issue 2; located at http://www.biomedcentral.com/1471-2431/1/2; Hochhaus, et al., licensee BioMed Central Ltd.; printed on Mar. 9, 2005.

Huang, Eric J; and Reichardt, Louis F.; "Neurotrophins: Roles in Neuronal Development and Function"; Annu. Rev. Neurosci. 2001; pp. 677-738; vol. 24; printed on Mar. 9, 2005.

Izumikawa, Masahiko; Minoda, Ryosei; Kawamoto, Kohei; Abrashiun, Karen A; Swiderski, Donald L; Dolan, David F; Brough, Douglas E.; and Raphael, Yehoash; "Auditory Hair Cell Replacement and Hearing Improvement by Atoh1 Gene Therapy in Deaf Mammals"; Nature Medicine 2005; pp. 1-6; Nature Publishing Group; printed on Mar. 29, 2005.

Kawamoto, Kohei; Ishimoto, Shin-Ichl Minoda, Ryosei; Brough, Douglas E.; and Raphael, Yehoash; "*Math1* Gene Transfer Generates New Cochlear Hair Cells in Mature Guinea Pigs In Vivo"; The Journal of Neuroscience; bearing a date of Jun. 1, 2003; pp. 4395-4400; vol. 23; Issue 11; printed on Mar. 9, 2005.

Langer, Robert; and Folkman, Judah; "Controlled Release of Macromolecules From Polymers"; Biomedical Polymers—Polymeric Materials and Pharmaceuticals for Biomedical Use; bearing a date of 1980; pp. 113-137; Eugene P. Goldberg and Akio Nakajima (eds.); Academic Press, Inc.

LaVan, David A; McGuire, Terry; and Langer, Robert; "Small-Scale Systems for In Vivo Drug Delivery"; Nature Biotechnology Review; Oct. 2003; pp. 1184-1191; vol. 21, No. 10; Nature Publishing Group; printed on Mar. 9, 2005.

Margalit, Eyal; Sadda,and Srinivas R.; "Retinal and Optic Nerve Diseases"; Artificial Organs; 2003; pp. 963-974; vol. 27, No. 11; Blackwell Publishing, Inc.; located at: http://www.blackwell-synergy.com/links/doi/10.1046/j.1525-1594.2003.07304.x/full/; printed on Mar. 18, 2005.

Marzella, Phillip L; Gillespie, Lisa N; "Role of Trophic Factors in the Development, Survival and Repair of Primary Auditory Neurons"; Clinical and Experimental Pharmacology and Physiology; bearing dates May 2002 and Jun. 2002; http://www.blackwell-synergy.com/links/do1/10.1046/j.1440-1681.2002.03684.x/abs/; printed on Mar. 17, 2005.

McAllister, A. Kimberley; Katz, Lawrence C.; and Lo, Donald C.; "Neurotrophins and Synaptic Plasticity"; Annu. Rev. Neurosci.; bearing a date of 1999; pp. 295-318; vol. 22; printed on Mar. 9, 2005.

Montcouquiol, Mireille; and Corwin, Jeffrey T.; "Brief Treatments with Forskolin Enhance S-Phase Entry in Balance Epithelia from the Ears of Rats"; The Journal of Neuroscience; Feb. 1, 2001; pp. 974-982; vol. 21; No. 3; Society for Neuroscience; printed on Mar. 9, 2005.

Pardridge, William M.; Kang, Young-Sook; and Buciak, Jody L.; "Transport of Human Recombinant Brain-Derived Neurotrophic Factor (BDNF) Through the Rat Blood-Brain Barrier in Vivo Using Vector-Mediated Peptide Drug Delivery"; Pharmaceutical Research; bearing dates of Oct. 7, 1993; Nov. 29, 1993; and 1994; pp. 738-746; vol. 11, No. 5; Plenum Publishing Corporation; printed on Mar. 9, 2005.

Perry, Martin J; and Higgs, Gerald A; "Chemotherapeutic Potential of Phosphodiesterase Inhibitors"; Current Opinion in Chemical Biology; 1998; pp. 472-481; vol. 2; located at: http://biomednet.com/elecref/1367593100200472; Current Biology Publications.

Petruska, Jeffery C.; and Mendell, Lorne M.; "The Many Functions of Nerve Growth Factor: Multiple Actions on Nociceptors"; Neuroscience Letters 361; 2004; pp. 168-171; located at : www.elsevier.com/locate/neulet; Elsevier Ireland Ltd.

Poo, Mu-Ming; "Neurotrophins as Synaptic Modulators"; Nature Reviews/Neuroscience; bearing a date of Jan. 2001; pp. 24-32; vol. 2; Macmillan Magazines Ltd.; printed on Mar. 9, 2005.

Rautioa, Jarkko; and Chikhale, Prashant J.; "Drug Delivery Systems for Brain Tumor Therapy"; Current Pharmaceutical Design; May 2004; pp. 1341-1353; vol. 10, No. 12; located at : http://www.ingentaconnect.com/content/ben/cpd/2004/00000010/00000012/art00006;jsessionid=ldwsqvra44e39.henrietta; printed on Jun. 6, 2005.

"Regeneration"; THESCIZONE.COM: The Spinal Cord Zone; bearing a date of Feb. 4, 2004; pp. 1-8; located at: http://www.thescizone.com/php/modules/wfsection/article.php?articleid=400; printed on Mar. 17, 2005.

"Remington's Pharmaceutical Sciences"; 18th Edition; bearing a date of 1990; A.R. Gennaro, ed.; Mack Printing Co., Easton, Pennsylvania.

Rhine, William D.; Hsieh, Dean S. T.; and Langer, Robert; "Polymers for Sustained Macromolecule Release: Procedures to Fabricate Reproducible Delivery Systems and Control Release Kinetics"; Journal of Pharmaceutical Sciences; bearing a date of Mar. 1980; pp. 265-270; vol. 69, No. 3; American Pharmaceutical Association.

Rydel, Russell E. and Greene, Lloyd A.; "cAMP Analogs Promote Survival and Neurite Outgrowth in Cultures of Rat Sympathetic and Sensory Neurons Independently of Nerve Growth Factor"; Proc. Natl. Acad. Sci. USA—Neurobiology; bearing dates of Feb. 1988, Sep. 8, 1987 and May 8, 1987; pp. 1257-1261; vol. 85.

Saragovi, H. Uri and Gehring, Kalle; "Development of Pharmacological Agents for Targeting Neurotrophins and Their Receptors"; TiPS—Review; bearing a date of Mar. 2000; pp. 93-98; vol. 21; Elsevier Science Ltd.

Saulnier, Beth; "Size Matters (Smaller Is Better)"; Cornell-Magazine On / Line; bearing dates of Jan. 2001 and Feb. 2001; pp. 1-11; vol. 103, No. 4; located at: http://cornell-magazine.cornell.edu/Archive/Jan2001/SizeMatters.html#top; printed on Mar. 17, 2005.

Sofroniew, Michael V.; Howe, Charles L.; and Mobley, William C.; "Nerve Growth Factor Signaling, Neuroprotection, and Neural Repair"; Annu. Rev. Neurosci.; bearing a date of 2001; pp. 1217-1281; vol. 24; Annual Reviews.

Spencer, Tim and Filbin, Marie T; "A Role for cAMP in Regeneration of the Adult Mammalian CNS"; J. Anat.—Review; bearing dates of Oct. 28, 2003 and 2004; pp. 49-55; vol. 204; Anatomical Society of Great Britain and Ireland.

Thoenen, Hans and Sendtner, Michael; "Neurotrophins: From Enthusiastic Expectations Through Sobering Experiences to Rational Therapeutic Approaches"; Nature Neuroscience Supplement—Review; bearing dates of Oct. 28, 2002 and Nov. 2002; pp. 1046-1050; vol. 5; Nature Publishing Group.

"To Restore Hearing—Abstracts"; The 36$^{TH}$ Karolinska Institutet Nobel Conference in Krusenberg, Sweden; bearing dates of Jun. 9-13, 2002; pp. 1-40; Center for Hearing and Communication Research, Karolinska Institutet & Karolinska Hospital; located at http://www.ki.se/cfh/images_inst/To%20Restore%20Hearing%202002.pdf; printed on Mar. 9, 2005.

Wang, J.; Van De Water, T. R.; Bonny, C.; De Ribaupierre, F.; Puel, J. L.; and Zine, A.; "A Peptide Inhibitor of c-Jun N-Terminal Kinase Protects Against Both Aminoglycoside and Acoustic Trauma-Induced Auditory Hair Cell Death and Hearing Loss"; The Journal of Neuroscience; bearing a date of Sep. 17, 2003; pp. 8596-8607; vol. 23; Issue 24; Society for Neuroscience.

Wu, Dafang and Pardridge, William M.; "Neuroprotection With Noninvasive Neurotrophin Delivery to the Brain"; Proc. Natl. Acad. Sci. USA—Neurobiology; bearing a date of Jan. 1999; pp. 254-259; vol. 96; The National Academy of Sciences.

Smolinske, Susan C.; "CRC Handbook of Food, Drug, and Cosmetic Excipients"; 1992; CRC Press, Inc.

Barinaga, Marcia; Neurotrophic Factors Enter the Clinic—The biotech industry launches a new class of nerve-nurturing drugs with high hopes of toppling stubborn neurological diseases such as Lou Gehrig's disease; Science—Research News; May 6, 1994; pp. 772-774; vol. 264; The American Association for the Advancement of Science.

Brew, Keith; Dinakarpandian, Deendayal; Nagase, Hideaki; Tissue Inhibitors of Metalloproteinases: evolution, structure and function; Biochimica et Biophysica Acta; bearing dates of Nov. 1, 1999, Dec. 1, 1999 and 2000; pp. 267-283; vol. 1477; Elsevier Science B.V.

Bruno, Martin A. and Cuello, A. Claudio; Activity-dependent release of precursor nerve growth factor, conversion to mature nerve growth factor, and its degradation by a protease cascade; PNAS—Neuroscience; Apr. 25, 2006; pp. 6735-6740; vol. 103; No. 17; The National Academy of Sciences of the U.S.A.

Cosgaya, Jose M.; Chan, Jonah R.; and Shooter, Eric M.; The Neurotrophin Receptor p75$^{NTR}$ as a Positive Modulator of Myelination; Science; Nov. 8, 2002; pp. 1245-1248; vol. 298; The American Association for the Advancement of Science.

Eng, Marian; Ling, Victor; Briggs, Jonathan A.; Souza, Karen; Canova-Davis, Eleanor; Powell, Michael F.; DeYoung, Linda R.; Formulation Development and Primary Degradation Pathways for Recombinant Human Nerve Growth Factor; Analytical Chemistry; Oct. 15, 1997; pp. 4184-4190; vol. 69; No. 20; American Chemical Society.

Kasaian, Marian T. and Neet, Kenneth E.; Internalization of Nerve Growth Factor by PC12 Cells—A Description of Cellular Pools; The Journal of Biological Chemistry; Apr. 15, 1988; pp. 5083-5090; vol. 263; No. 11; The American Society for Biochemistry and Molecular Biology, Inc.

Lee, Ramee; Kermani, Pouneh; Teng, Kenneth K.; Hempstead, Barbara L.; Regulation of Cell Survival by Secreted Proneurotrophins; Science; Nov. 30, 2001; pp. 1945-1948; The American Association for the Advancement of Science.

Pang; Petti T.; Teng, Henry K.; Zaitsev, Eugene; Woo, Newton T.; Sakata, Kazuko; Zhen, Shushuang; Teng, Kenneth K.; Yung, Wing-Ho; Hempstead, Barbara L.; and Lu, Bai; Cleavage of proBDNF by tPA/Plasmin Is Essential for Long-Term Hippocampal Plasticity; Science; Oct. 15, 2004; pp. 487-491; vol. 306; The American Association for the Advancement of Science.

U.S. Appl. No. 11/891,373, Ishikawa et al.
U.S. Appl. No. 11/891,372, Ishikawa et al.
U.S. Appl. No. 11/891,336, Ishikawa et al.
U.S. Appl. No. 11/891,335, Ishikawa et al.
U.S. Appl. No. 11/891,321, Ishikawa et al.

Gillespie, Lisa N.; Clark, Graeme M.; Bartlett, Perry F.; Marzella, Phillip L.; BDNF-Induced Survival of Auditory Neurons In Vivo: Cessation of Treatment Leads to Accelerated Loss of Survival Effects; Journal of Neuroscience Research; bearing dates of Aug. 22, 2002, Nov. 7, 2002, Nov. 8, 2002 and 2003; pp. 785-790; vol. 71; Wiley-Liss, Inc.

Ruan, Run Sheng; Leong, Seng Kee; Mark, Ignatius; Yeoh, Kian Hian; Effects of BDNF and NT-3 on hair cell survival in guinea pig cochlea damaged by kanamycin treatment; NeuroReport; Jul. 13, 1999; pp. 2067-2071; vol. 10; No. 10; Lippincott Williams & Wilkins.

Holz, Frank G.; Pauleikhoff, Daniel; Klein, Ronald; and Bird, Alan C.; "Pathogenesis of Lesions in Late Age-related Macular Disease"; American Journal of Ophthalmology; Bearing a date of Mar. 2004; pp. 504-510; vol. 137, No. 3; Elsevier Inc.

Reichardt, Louis F.; and Mobley, William C.; "Going the Distance, or Not, with Neurotrophin Signals"; Cell; Bearing a date of Jul. 23, 2004; pp. 141-143; vol. 118; Cell Press.

Rudolphi, Karl A.; and Schubert, Peter; "Modulation of neuronal and glial cell function by adenosine and neuroprotection in vascular dementia"; Behavioural Brain Research; Bearing dates of Sep. 18, 1995, Nov. 9, 1995, and 1997; pp. 123-128; vol. 83; Elsevier Science B.V.

Sugino, Ilene K.; Wang, Hao; and Zarbin, Marco a.; "Age-Related Macular Degeneration and Retinal Pigment Epithelium Wound Healing"; Molecular Neurobiology; Bearing dates of 2003, and Feb. 24, 2003; pp. 177-194; vol. 28, No. 2; Humana Press Inc.

Zarbin, Marco A.; "Current Concepts in the Pathogenesis of Age-Related Macular Degeneration"; Archives of Ophthalmology; Bearing dates of 2004, and Apr. 2004; pp. 598-614; vol. 122; American Medical Association.

Chen, Biao, et al.; "Increased Hippocampal BDNF Immunoreactivity in Subjects Treated with Antidepressant Medication"; Biological Psychiatry; Bearing a date of 2001; pp. 260-265; vol. 50; Society of Biological Psychiatry.

Cui, Qi, et al.; "Intraocular elevation of cyclic AMP potentiates ciliary neurotrophic factor-induced regeneration of adult rat retinal ganglion cell axons"; Molecular and Cellular Neuroscience; Bearing a date of 2003; pp. 49-61; vol. 22; Elsevier Science (USA).

Fujimaki, Koichiro, et al.; "Administration of a cAMP Phosphodiesterase 4 Inhibitor Enhances Antidepressant-Induction of BDNF mRNA in Rat Hippocampus"; Neuropsychopharmacology; Bearing a date of 2000; pp. 42-51; vol. 22, No. 1; Elsevier Science Inc.

Karege, Félicien, et al.; "Decreased serum brain-derived neurotrophic factor levels in major depressed patients"; Psychiatry Research; Bearing a date of 2002; pp. 143-148; vol. 109; Elsevier Science Ireland Ltd.

Katoh-Semba, Ritsuko, et al.; "A phase advance of the light-dark cycle stimulates production of BDNF, but not of other neurotrophins, in the adult rat cerebral cortex: association with the activation of CREB"; Journal of Neurochemistry; Bearing a date of 2008; pp. 2131-2142; vol. 106; International Society for Neurochemistry.

Nikulina, Elena, et al.; "The phosphodiesterase inhibitor rolipram delivered after a spinal cord lesion promotes axonal regeneration and functional recovery"; PNAS; Bearing a date of Jun. 8, 2004; pp. 8786-8790; vol. 101, No. 23; The National Academy of Sciences of the USA.

Siuciak, Judith A., et al.; "Antidepressant-Like Effect of Brain-derived Neurotrophic Factor (BDNF)"; Pharmacology Biochemistry and Behavior; Bearing a date of 1997; pp. 131-137; vol. 56, No. 1; Elsevier Science Inc.

The State Intellectual Property Office of the People's Republic of China; Application No. 200680025687.8; bearing a date of Jun. 17, 2010; pp. 1-22.

Lau, H. Y. A. et al.; "Modulation of intracellular cyclic AMP in immunologically activated rat peritoneal mast cells by prostaglandin $D_2$"; Inflammation Research; bearing a date of 2001; pp. S61-S62; vol. 50, Supplement 2; Birkhauser Verlag, Basel, 2001.

Supplementary European Search Report; European Application No. 06 77 2872; pp. 1-8; Nov. 29, 2011 (Received by our agent Dec. 5, 2011).

Bergsma, Donald R.; "Retinal Damage, Protection, and Repair"; Molecular Neurobiology; Bearing a date of 2003; pp. 107-109; vol. 28, No. 2; Humana Press Inc.

Dal Piaz, Vittorio; and Giovannoni, Maria Paola; "Phosphodiesterase 4 inhibitors, structurally unrelated to Rolipram, as promising agents for the treatment of asthma and other pathologies"; European Journal of Medicinal Chemistry; Bearing dates of 2000, and Feb. 28, 2000; pp. 463-480; vol. 35; Éditions scientifiques et médicales Elsevier SAS.

Ethier, C. Ross; Johnson, Mark; and Ruberti, Jeff; "Ocular Biomechanics and Biotransport"; Annual Review of Biomedical Engineering; Bearing dates of 2004, and Feb. 6, 2004; pp. 249-273 plus two pages; vol. 6; Annual Reviews.

* cited by examiner

METHODS FOR ELEVATING NEUROTROPHIC AGENTS

TECHNICAL FIELD

The present application relates, in general, to methods and systems for modulating the concentration of neurotrophins within or in the vicinity of neural tissues.

SUMMARY

Exemplary methods and systems are described for modulating the concentration of one or more neurotrophins within or in the vicinity of neural tissues. In one aspect, a method includes elevating the concentration of at least one neurotrophin within a neural tissue of a mammal and elevating the concentration of at least one inhibitor of degradation of the neurotrophin within the neural tissue. In some aspects, the method includes regulating the concentration of the neurotrophin over time and/or monitoring the concentration of the neurotrophin over time.

In one aspect, a system includes a neurotrophin release device capable of releasing a neurotrophin within or in the vicinity of a neural tissue. In another aspect, the system includes an inhibitor release device capable of releasing an inhibitor of degradation of the neurotrophin. The system may include one or more sensors capable of sensing the concentration of a neurotrophin and/or an inhibitor and a controller for controlling the release of neurotrophin and/or inhibitor of neurotrophin degradation. Certain embodiments may include the capability of transmitting data to a remote device for display and evaluation, and/or for receiving control signals from a remote device.

The foregoing is a summary and thus contains, by necessity, simplifications, generalizations and omissions of detail; consequently, those skilled in the art will appreciate that the summary is illustrative only and is not intended to be in any way limiting. Various additional aspects of the inventive method and system are set forth and described in the claims, drawings, and text forming a part of the present application. Other aspects and advantages of the methods and systems described herein, as defined solely by the claims, will become apparent in the detailed description set forth herein.

BRIEF DESCRIPTION OF THE FIGURES

The use of the same symbols in different drawings typically indicates similar or identical items.

DETAILED DESCRIPTION

Figure 1:
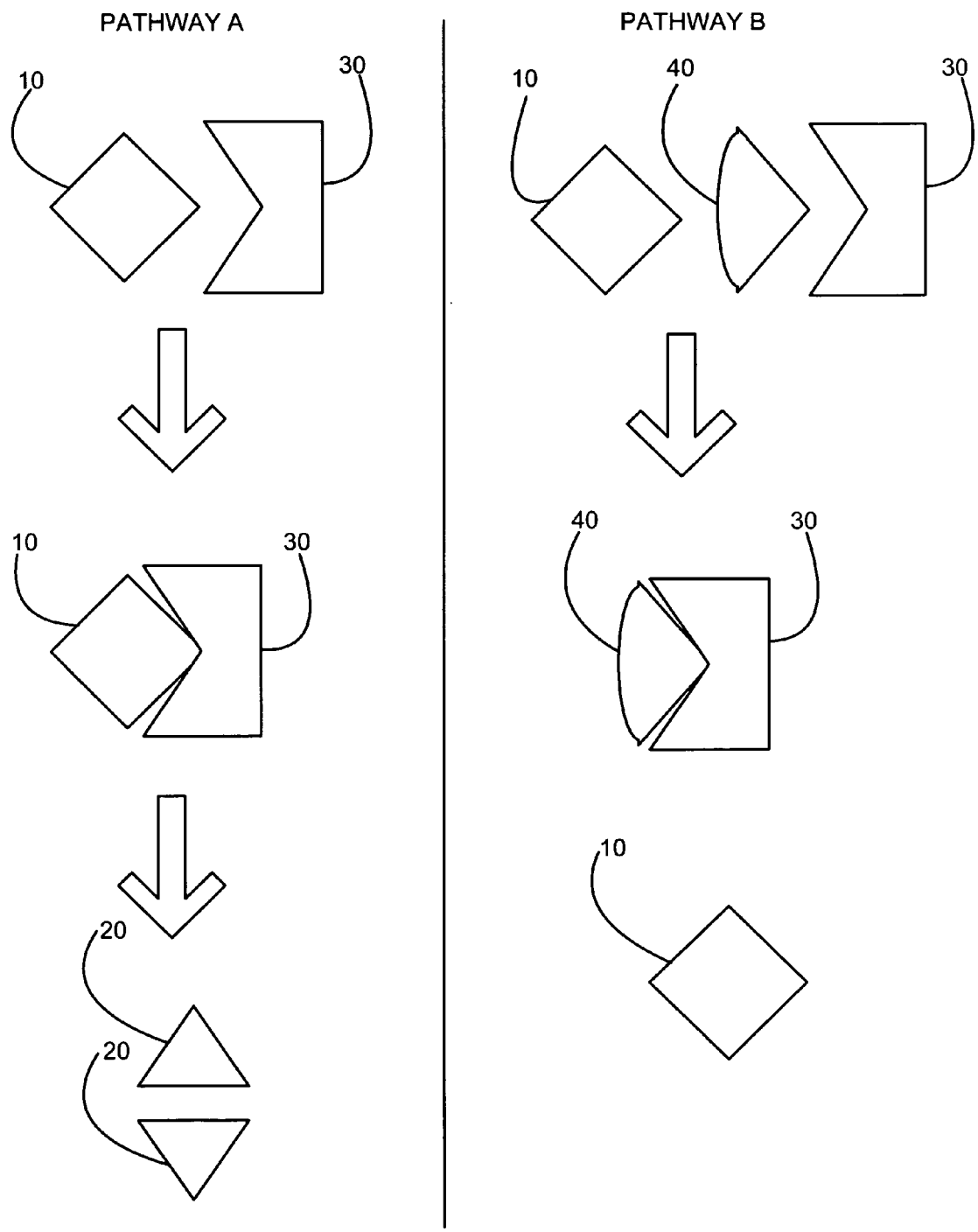
FIG. 1A illustrates a mechanism of degradation of a neurotrophin.
FIG. 1B illustrates an inhibition of the neurotrophin degradation mechanism that is illustrated in FIG. 1A.

Methods and systems as described and illustrated herein are thought to be particularly beneficial with regard to preservation, restoration or enhancement of sensory function, but they are not limited to these applications. Sensory tissues that may be beneficially treated include, but are not limited to, auditory, olfactory, visual, and somatosensory structures such as the cochlea, olfactory bulb, and retina. In addition, structures of both the central and peripheral nervous systems may be treated with regard to preservation, restoration or enhancement by the methods and systems described herein. In some embodiments, the methods and systems described herein may find application in the treatment of neurons damaged though injury, including injuries sustained during surgery. In some embodiments, the methods and systems described herein may find application in conjunction with neural tissue grafts, implants or related surgical therapies. In some embodiments, the methods and systems described herein may find application in testing patient response to neurotrophins for diagnostic and/or therapeutic purposes. In some embodiments, the methods and systems described herein may find application in monitoring patient status over time and/or acting in conjunction with other therapies. While the concentration(s) of neurotrophin(s) may be modulated in a wide variety of organisms, it is contemplated that methods and systems as described and illustrated herein will find greatest application in humans and selected non-human mammals. Some embodiments, for instance, may find application in a domesticated mammal such as a dog, cat, horse, cow, sheep or goat.

As used herein, the term "neurotrophin" refers to any biochemical agent that results in an increase in neuronal metabolic activity, mitotic activity, growth, differentiation or survival when it is introduced into or in the vicinity of a neuron. The effects on a neuron generated by a neurotrophin are "neurotrophic" effects. Neurotrophins may include either or both endogenous substances which are naturally present in some tissue at some stage of life and non-endogenous substances which exhibit neurotrophic effects. A neurotrophin may be any molecule or biological complex which has neurotrophic effects and may, for example, include peptides, proteins, protein complexes, cyclic nucleoside monophosphates or hormones. For example, proteins with established neurotrophic activities include: nerve growth factor (NGF), brain-derived neurotrophic factor (BDNF), neurotrophin-3 (NT-3), neurotrophin 4/5 (NT-4/5), ciliary neurotrophic factor (CNTF), leukemia inhibitory factor/cholinergic differentiation factor (LIF/CDF), cardiotrophin-1, basic fibroblast growth factor (bFGF), acidic fibroblast growth factor (aFGF), fibroblast growth factor-5 (FGF-5), insulin, insulin-like growth factor I (IGF-I), insulin-like growth factor Ii (IGF-II), transforming growth factor $\beta 1$ (TGF $\beta 1$), transforming growth factor $\beta 2$ (TGF $\beta 2$), transforming growth factor $\beta 3$ (TGF $\beta 3$), activin, glial cell-derived neurotrophic factor (GDNF), midkine, heparin-binding neurotrophic factor (HBNF), pleiotrophin, epidermal growth factor (EGF), transforming growth factor $\alpha$ (TGF $\alpha$), schwannoma-derived growth factor, heregulin (neuroregulin, ARIA), interleukin 1, interleukin 2, interleukin 3, interleukin 6, axon ligand-1 (A1-1), elf-1, ehk1-L, or LERK2. Neurotrophin also refers to both what is commonly referred to as the neurotrophin protein family (e.g. nerve growth factor (NGF), neurotrophin-3 (NT-3) etc.) as well as other factors with neurotrophic effects. Exemplary neurotrophins include NGF, brain derived neurotrophic factor (BDNF), NT-3, neurotrophin 4 (NT-4), neurotrophin-6 (NT-6), or neurotrophin-7 (NT-7), adenosine 3', 5'-cyclic monophosphate (cAMP), and the like, and derivatives or analogues thereof and in any combination thereof. See e.g. Hefti, Ann. Rev. Pharmacol. Toxicol., 37: 239-267, 1997, Cai et al., J. Neurosci., 21(13): 4731-4739 (2001) and Huang and Reichardt, *Annu. Rev. Neurosci* 24:677-736, 2001. For example, cAMP derivatives and analogs include forskolin, dibutyric-cAMP (db-cAMP), adenosine 3',5'-cyclic monophosphate benzyl ester (cAMP-Bn), 8-chloroadenosine-3',5'-cyclic monophosphate (8-Cl-cAMP), and the like, or any agent that influences cAMP mediated metabolic pathways. See e.g. Rydel et al., PNAS 85, 1257-1261, 1988. In some situations, the neurotrophin may be a metabolic precursor of the biochemically active agent, in which case the neurotrophin precursor is susceptible to being altered by one or more endogenous metabolic factors to generate an active form of the neurotrophin. In some situations, more than one neurotrophin precursor molecule of the same or different type may combine or complex to form an active neurotrophin. A neurotrophin may be made up of several subunits or component parts which may be the same or different proteins, saccharides or other molecules. As a non-limiting example, biochemically functional NGF consists of a protein dimer (see e.g. Sofroniew et al., Annu. Rev. Neurosci. 24:1217-1281, 2001).

By way of background and not wishing to be bound by theory, neurotrophins have been shown to have many influences on cells at different times in the life cycle of an organism, including regulation of neural development, plasticity, function, maintenance and survival. See e.g. Huang and Reichardt, Annu. Rev. Neurosci 24:677-736, 2001; Petruska and Mendell, Neurosci. Lett. 361:168-171, 2004 and D'Sa et al., Bipolar Dis. 4:183-194, 2002. Multiple cells normally release neurotrophins during development and through the life cycle of an organism, including after injury. See e.g. Huang and Reichardt, Annu. Rev. Neurosci 24:677-736, 2001; Hochhaus et al., BMC Pediatrics 1:2, 2001; Spencer and Filbin, J. Anat. 204:49-55, 2004. Biochemically active neurotrophins may come from either endogenous or exogenous sources. For example, endogenous neurotrophins are produced by skin, vascular and smooth muscle cells, endocrine tissues and salivary glands during the normal life cycle of these cell types (reviewed in Sofroniew et al., Annu. Rev. Neurosci. 24:1217-1281, 2001). Exogenous neurotrophins have also been shown to have neuroprotective effects when supplied to the ischemic hippocampus (see e.g. Wu and Pardridge PNAS 96:254-259, 1999). Some antidepressants used in treating chronic depression have neurotrophic effects in the hippocampus (see e.g. Castren Curr. Opin. Pharma., 4:58-64, 2004 and D'Sa et al., Bipolar Dis. 4:183-194, 2002).

Both endogenous and exogenous neurotrophins typically do not persist indefinitely within the body of an organism, but are degraded by neurotrophin degrading agents. In some embodiments, the inhibitor of degradation may be erythro-9-(2-hydroxy-3-nonyl) adenine. In some embodiments, the inhibitor of degradation may be at least one of: milrinone, aminone, pimobendan, or enoximone. In some embodiments, the inhibitor of degradation may be at least one of: rolipram, Ro 20-1724, denbufylline, RS 25344, CP80633, SB207499, RP 73401, CDP 840, or zadarverine. In some embodiments, the inhibitor of degradation may be zaprinast. In some embodiments, the inhibitor of degradation may be dipyridimole. As used herein, the term "neurotrophin degrading agent" refers to any factor that directly or indirectly causes a chemical, structural, or functional alteration to a neurotrophin, which results in a reduction in the neurotrophin's basal neurotrophic activity. This chemical, structural, or functional alteration may be permanent or it may be transitory. A neurotrophin degrading agent is any molecule or biological complex which has neurotrophin degrading effects and may, by way of non-limiting examples, include peptides, proteins, protein complexes, enzymes, antibodies or hormones. Substances which function as neurotrophin degrading agents can be naturally present within living organisms, and influence the concentration of neurotrophins within cells or tissues of the organisms. In some embodiments, the neurotrophin degrading agent is an enzyme. In addition, there exist "inhibitors of neurotrophin degradation", which can be any factor that cause directly or indirectly chemical, structural, or functional alteration(s) to a neurotrophin degrading agent resulting in a reduction in its basal activity. This chemical, structural, or functional alteration may be permanent or it may be transitory. The inhibitor of degradation may be a peptide, a protein, an antibody, a chemical or other factor or combination thereof that reduces the activity of a neurotrophin degrading agent. In one exemplary embodiment, the neurotrophin may be cAMP, the neurotrophin degrading agent may be a phosphodiesterase, such as PDE4, and the inhibitor of degradation may be 4-[3-(Cyclopentyloxy)-4-methoxy-phenyl]-2-pyrrolidinone (rolipram) (see e.g., Perry and Higgs, Curr. Opin. Chem. Bio. 2: 472-481, 1998).

As used herein, the term "neural tissue" refers to both central and peripheral nervous system components, and to tissues and structures within the body which include or are associated with one or more neuronal components, but are not necessarily themselves neuronal or of neural origin. These include "highly innervated tissues", which are tissues that contain, are supplied by, or are innervated by large numbers of nerve cells or processes either efferent or afferent. Examples of highly innervated tissues include the cochlea, the olfactory bulb and the retina. Highly innervated tissues are not limited to the specific examples listed herein and include tissues that contain a large number of somatosensory fibers such as portions of the skin, bones, muscle, or joint capsules, or tissues or organs that are under direct neural regulation such as certain glandular tissues and portions of the digestive system. In some cases, the concentration of neurotrophin may be elevated within a sensory organ, which is any tissue that detects stimuli from the environment. Examples of sensory organs include the eye, ear, nose and tongue. The concentration of neurotrophin may be elevated in the entire sensory organ and/or within a "therapeutically effective region" of it. As used herein, the term "therapeutically effective region" refers to a region which allows for transfer of the introduced agent by active or passive means to the cells of interest in the particular situation. In some situations, the therapeutically effective region is within or immediately adjacent to a highly innervated tissue, while in others it may be at some distance within the body (see e.g., Montcouquiol and Corwin, J Neurosci., 21(3):974-982, 2001; Castren Mol. Neurobio., 29:289-301, 2004).

As used herein, the term "neural support tissue" refers to tissues and cells which give at least one neuron physical, physiological or metabolic support. Examples of neural support tissues include glial cells such as oligodendrocytes, Schwann cells and astrocytes, and vascular structures in the region of a neuron. In many situations, neural support tissue is located in the region or vicinity of a neuron, but in some cases it may be located in another region of the body and support the neuron metabolically or physiologically by directly producing or indirectly causing the production of neural support substances. In some situations a neural support tissue produces at least one "neural support substance", which is a substance that acts to support the neuron metabolically or physiologically and acts either regionally or at a distance within the body. Examples of neural support substances include neurotrophins, neuron apoptosis inhibitors, suppressors of inflammatory responses that may damage neurons, suppressors of autoimmune factors that may damage neurons and neuronal survival promoters such as anti-beta (β) amyloid antibodies.

Pathway A of FIG. 1 illustrates an exemplary mechanism for degradation of a neurotrophin 10 by a degrading agent 30. Pathway A depicts a physiological process whereby the neurotrophin 10 binds to the degrading agent 30 to produce neurotrophin degradation products 20, which may be inactive or degraded neurotrophin. Depending on the particular neurotrophin and degrading agent, they may bind irreversibly and be degraded together or only the neurotrophin may be degraded and the degrading agent may be released intact. The degrading agent may also retain some portion of the original neurotrophin molecule after another portion is released. More than one unit of the degrading agent may also bind to more than one unit of the neurotrophin. A unit of the neurotrophin and/or the degrading agent may be a complex of multiple molecules or a single molecule, depending on the embodiment.

As depicted in pathway B of FIG. 1, when an inhibitor of degradation 40 is present, neurotrophin degrading agent 30 may bind to inhibitor of degradation 40, resulting in a reduction in neurotrophin degrading activity. Although a single-molecule inhibitor of degradation is depicted diagrammatically in FIG. 1, the inhibitor may be comprised of a single molecule, multiple molecules or a chemical compound which in the aggregate results in an inhibition of the degradation of the neurotrophin. In some embodiments, the neurotrophin degrading agent is irreversibly bound to the inhibitor while in others the binding is transient. The inhibitor may chemically or structurally alter the degrading agent so that its degrading activity is reduced, or it may release the degrading agent unaltered after some time period or in response to a chemical reaction. The inhibitor may bind to the same molecular site on the degrading agent as the neurotrophin or it may bind to a different molecular site. The inhibitor of degradation may also bind directly to the neurotrophin.

One skilled in the art will appreciate that both pathways A and B (shown in FIG. 1) may operate simultaneously in the same cell or tissue. In this situation, by elevating the relative concentrations of neurotrophin and inhibitor of neurotrophin degradation, the relative activity of the two pathways and/or the total concentration of neurotrophin may be modulated. A person skilled in the art will appreciate that the presence of an inhibitor of degradation of the neurotrophin will not result in blocking the degradation of all neurotrophin molecules, and that events depicted in pathway A and events depicted in pathway B of FIG. 1 may both occur, although at different relative rates, in any given embodiment. The rates of either degradation of the neurotrophin or inhibition of degradation are dependent on several factors, including but not limited to the relative concentrations of the neurotrophin, the degrading agent and the inhibitor of degradation as well as the kinetic activity of each. As used herein, the term "concentration" refers to the molar quantity of a molecule or compound and/or its biochemical analogs in a region which may be a cell, a subcellular region, a tissue or a location in the vicinity of one of these. The "level" of a neurotrophin and/or an inhibitor of degradation of a neurotrophin is the concentration within a localized region such as within a sensory organ, a highly innervated tissue or other relevant region. As will be understood by one skilled in the art, the concentrations of neurotrophin, inhibitor of degradation of the neurotrophin and degrading agent are likely to be interdependent in any given embodiment and vary over time. Therefore while it is possible to modulate and/or control the levels of neurotrophin and/or inhibitor of degradation of neurotrophin to some degree, the concentration of both of these substances will be inherently dynamic in any given situation.

In various embodiments, neurotrophins and inhibitors of neurotrophin degradation may be introduced into therapeutically effective region(s). While elevating the levels of neurotrophin may ultimately affect a specific cell or group of cells, it is not required that the neurotrophin be delivered into the cell or cells to be affected, nor is it necessary that the concentration of neurotrophin within the cell or cells be measured directly. As will be understood by one skilled in the art, the elevation of the concentration of one or more neurotrophins and/or one or more inhibitors of degradation of a neurotrophin and/or one or more neural support substances in the vicinity of a neural tissue or highly innervated tissue within the body of a mammal may result in the elevation of the concentration of neurotrophin within the tissue or cells within the tissue. In some embodiments, therefore, a "point of release" or multiple points of release either within or in the vicinity of the tissue may be effective to modulate the concentration of neurotrophin as desired. As used herein, a "point of release" is the location where the substance is primarily released into the body. In some embodiments, the point of release is where the substance is physically released into the body, while in others the point of release is where the substance is metabolized into its biochemically active form. Introduced neurotrophins may be identical to endogenously produced neurotrophins, or may be analogs of endogenous neurotrophins, and may be structurally similar, functionally similar, or both. Moreover, substances that may be introduced include substances that are precursors or components of neurotrophins which, upon delivery into a neural tissue, are altered by endogenous factors to produce a neurotrophin, such that an increase in the concentration of the released substance in the tissue produces a corresponding increase in concentration of the neurotrophin. In some embodiments, the substance or substances will be released once while in others they will be released on multiple occasions. In some embodiments, more than one neurotrophin and/or more than one inhibitor of degradation and/or more than one neural support substance will be released in order to attain the desired effects. More than one release strategy may be effective or desired in any given situation. Methods and systems as illustrated herein may operate to modulate neurotrophin concentrations to or toward normal levels (i.e., in subjects having initially lower than normal neurotrophin levels), or to modulate neurotrophin levels beyond physiological concentration levels.

Figure 2:
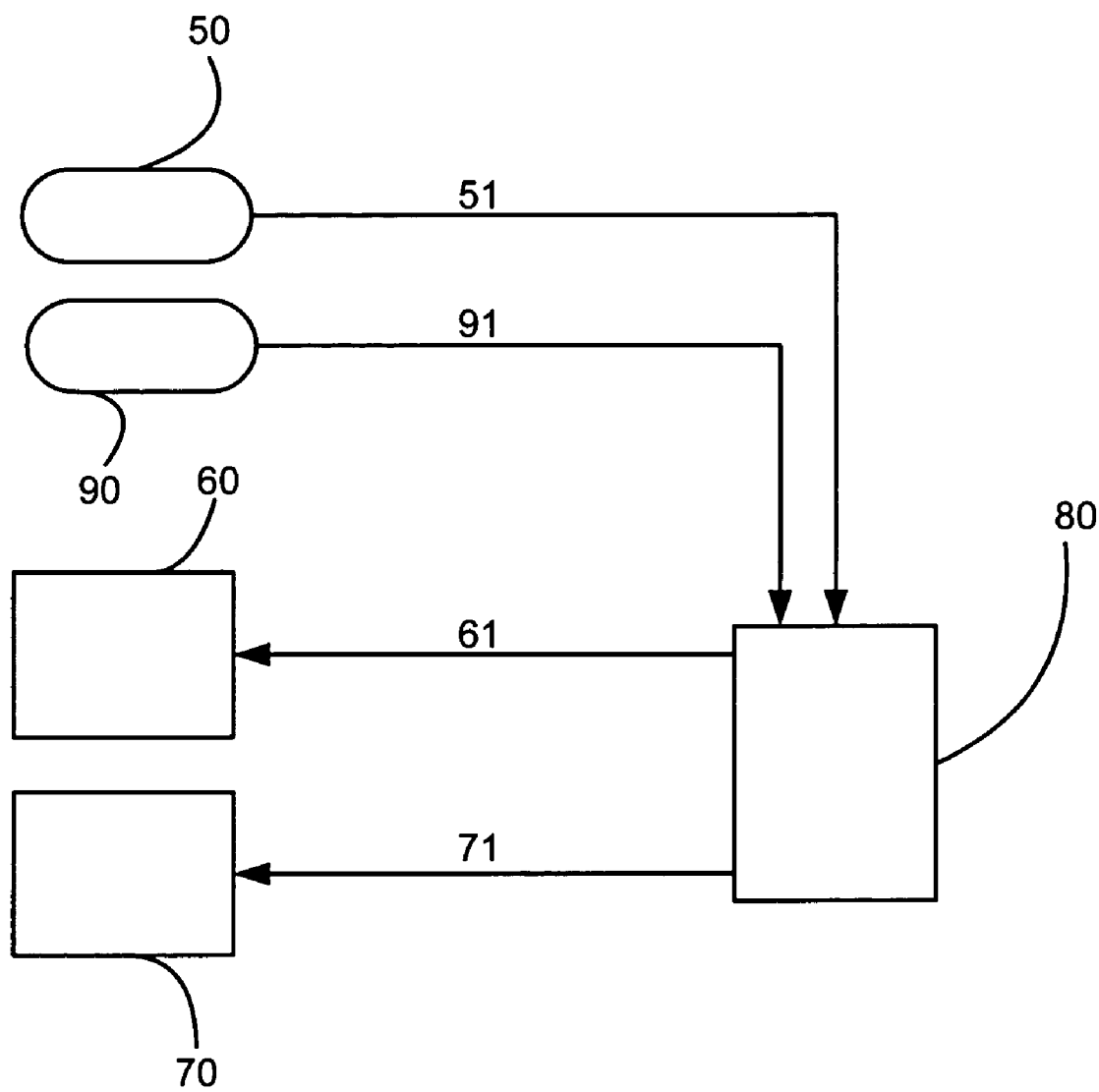
FIG. 2 illustrates an embodiment of a system for modulating levels of a neurotrophin.

The simplified exemplary system of FIG. 2 includes an implantable neurotrophin release device 60 capable of releasing a neurotrophin and an implantable inhibitor release device 70 capable of releasing an inhibitor of degradation of the neurotrophin. In many embodiments, the release devices may be implantable and present in the body for an extended time period such as days, weeks, months or years while in other embodiments the release devices are only present for a short time during treatment. Release devices 60 and 70 may be two separate devices, as illustrated in FIG. 2, or may be configured as a single device. In some embodiments there may be a plurality of release devices. Release devices 60 and 70 may be controlled release devices that include means to regulate the release of neurotrophin and/or at least one inhibitor of degradation, respectively, over time, in response to a control signal generated by controller 80. Controller 80 may be an electronic controller and may include a signal generator and/or a microprocessor. Controller 80 may be connected to the neurotrophin release device 60 and inhibitor release device 70 by any means known in the art, including electronic cabling, wireless or other connections. Controller 80 may generate at least one control signal that is transmitted to at least one of the neurotrophin release device and/or the inhibitor release device via said connection. Controller 80 may also be implantable or partially implantable in some applications.

In the simplified exemplary embodiment depicted in FIG. 2, controller 80 receives signals 51, 91 from neurotrophin sensor 50 and inhibitor sensor 90. The neurotrophin sensor 50 is capable of detecting a concentration of the neurotrophin, while inhibitor sensor 90 is capable of detecting a concentration of the inhibitor of neurotrophin degradation. Although 2 sensors are depicted in FIG. 2, in some embodiments there may be only one sensor or more than 2 sensors. In addition, multiple sensors may be integrated into a single device. Depending on the embodiment, the sensors may detect and quantify the concentrations of the relevant substance(s) and/or they may detect concentrations only at a particular level or range. In some embodiments the sensors detect induced activities from the release, such as a resulting biochemical reaction. The data from the sensors may be used to monitor the concentration of neurotrophin within the highly innervated tissue. Based upon the values of signals 51 and 91 from neurotrophin sensor 50 and inhibitor sensor 90, respectively, controller 80 determines a suitable modification to the release of neurotrophin and inhibitor of neurotrophin degradation in order to appropriately control the level of neurotrophin. Controller 80 then produces neurotrophin release device control signal 61, which is sent to neurotrophin release device 60 and inhibitor release device control signal 71, which is sent to inhibitor release device 70, to produce the desired modification to the activity of these devices.

Figure 3:
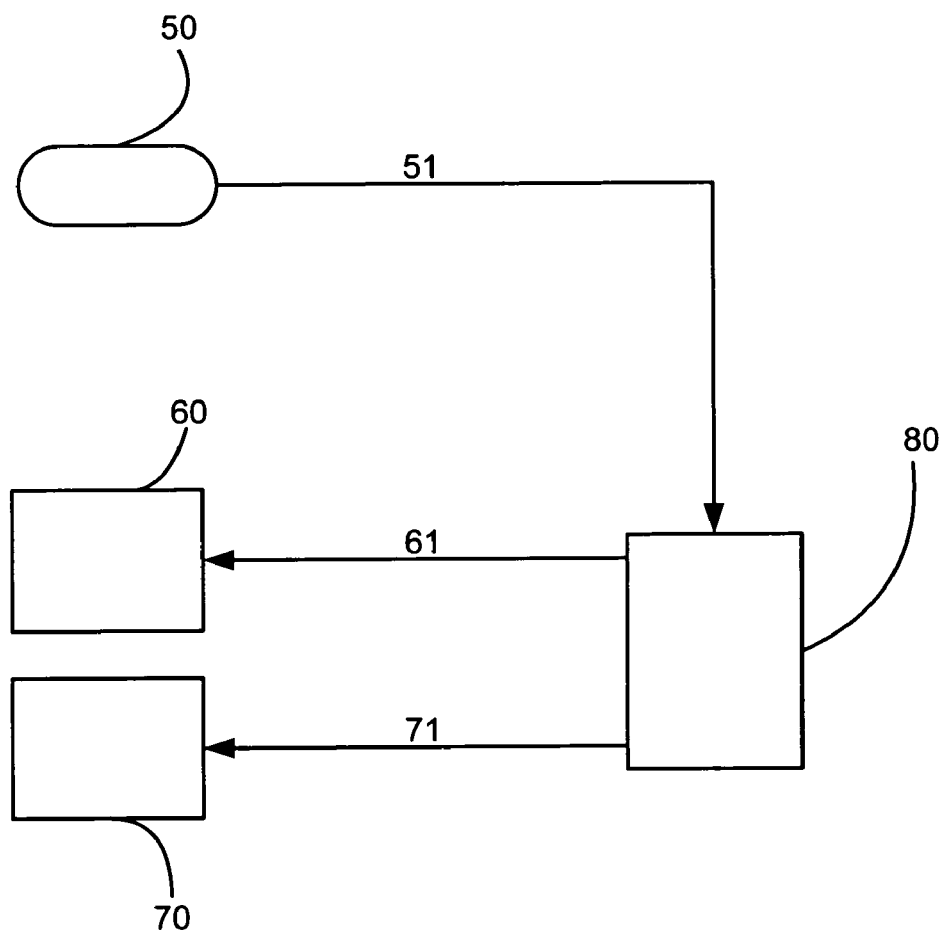
FIG. 3 illustrates an embodiment of a system including a remote device.
Figure 3:
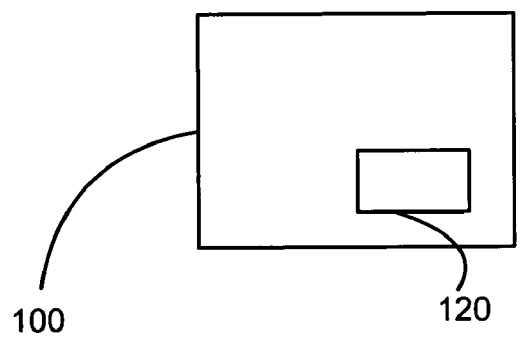

FIG. 3 depicts another exemplary embodiment of the system that includes neurotrophin release device 60, inhibitor release device 70, and controller 80. In this exemplary embodiment, a single neurotrophin sensor 50 provides a signal 51 to controller 80. In some embodiments the addition of more neurotrophin, the addition of an inhibitor of degradation of the neurotrophin or both may be regulated based on the sensor data. Operation of detectors 50 and release devices 60 and 70 are substantially as described in connection with FIG. 2. Also included is remote device 100, which may provide remote monitoring and/or control capabilities beyond those provided by controller 80. The remote device may be coupled to the sensor(s), the release device(s) and/or the controller. In some embodiments, the remote device 100 and the controller 80 may be combined into one device. Remote device 100 may be configured to allow a user to monitor the effects of the implanted system, to control the operation of the system, or both. The user may be the subject within whom the system sensor 50, release devices 60 and 70, and controller 80 are implanted, or another user such as a physician or other medical personnel.

The concentration of neurotrophin may also be graphically displayed through an imaging device or devices coupled to the controller. An imaging device may be a remote device 100 as depicted in FIG. 3. In some embodiments, an imaging device may be used to monitor the concentration of neurotrophin over time. An imaging device may be capable of imaging the levels of the neurotrophin or neurotrophin-induced biochemical activity within a therapeutically effective region of the sensory organ. Depending on the embodiment, the therapeutically effective region may comprise the cochlea, the olfactory bulb or the retina, or pertinent fractions thereof. The imaging device may be adapted to receive information from one or more sensors and capable of displaying information from at least one sensor. For example, remote device 100 may include an imaging device, a display device and/or an input device. A display device may be, for example, a computer monitor or various other display devices as are known in the art. In one aspect, remote device 100 may function as an imaging device and a display device that is capable of generating a graphical depiction of the neurotrophin concentration detected by the sensor device 50 as a function of time. Alternatively or in addition, remote device 100 may provide a numerical display specifying the detected concentration at the current time, or at some other time. A display device may be configured to display multiple parameters of interest simultaneously or a single parameter. Displayed parameters may include, for example, the detected concentration of neurotrophin, and/or the release rates of neurotrophin and inhibitor of neurotrophin degradation provided by release devices 60 and 70. Various display formats may be used as are known to those of skill in the art. Other displayed parameters may include various parameters relating to the control scheme used to regulate rates of release of substances from release devices 60 and 70.

The remote device may be user configurable to display user-selected parameters in a user-selected format. The remote device may be configured to display menus on a display device and to receive user input indicating the user's selection of menu options from an input device. An input device may include a keyboard, an instrument control panel, a microphone (in which case voice commands may be processed by voice recognition hardware or software), or various other input means well known to those of skill in the art. In some embodiments, there may be multiple remote devices located at the same or multiple locations, said remote devices of the same or different types. In some embodiments, display devices and input devices may be formed integrally as a touch-screen so that a single device may provide both display and input functions. In addition to selecting and controlling the display of data on a display device, the entry of commands at an input device may be used to change the configuration or programming of the controller. For example, in some embodiments the user may change the type of control scheme used to regulate rates of release of substances from the release device or devices such as by changing the target value from a constant stored value to a calculated value or by changing stored constants used in the control scheme.

It is contemplated that remote device 100 is located externally to the body of the subject in which sensors 50, 90 and release devices 60, 70 are implanted. As described in connection with the embodiment of FIG. 2, controller 80 may be implanted within the body of the subject, either in the vicinity of sensor 50 and release devices 60 and 70, or at some other location within the body, or may be external to the body. If controller 80 is external to the body, controller 80 and remote device 100 may be constructed as a single device. Remote device 100 may be connected to controller 80 by any means known in the art, including an electronic cable or a wireless connection. If remote device 100 is connected via an electronic cable, the connection may be made via a transdermal connector, as is known in the art. Such a connection method may be suitable for occasional uses of the system in combination with remote device 100 such as for intermittent medical monitoring or for experimental use. If continuous use of the system in combination with remote device 100 is desired, it may be preferable to connect remote device 100 with controller 80 via a wireless connection, such as via radio frequency, infrared or other wireless connections.

Figure 4:
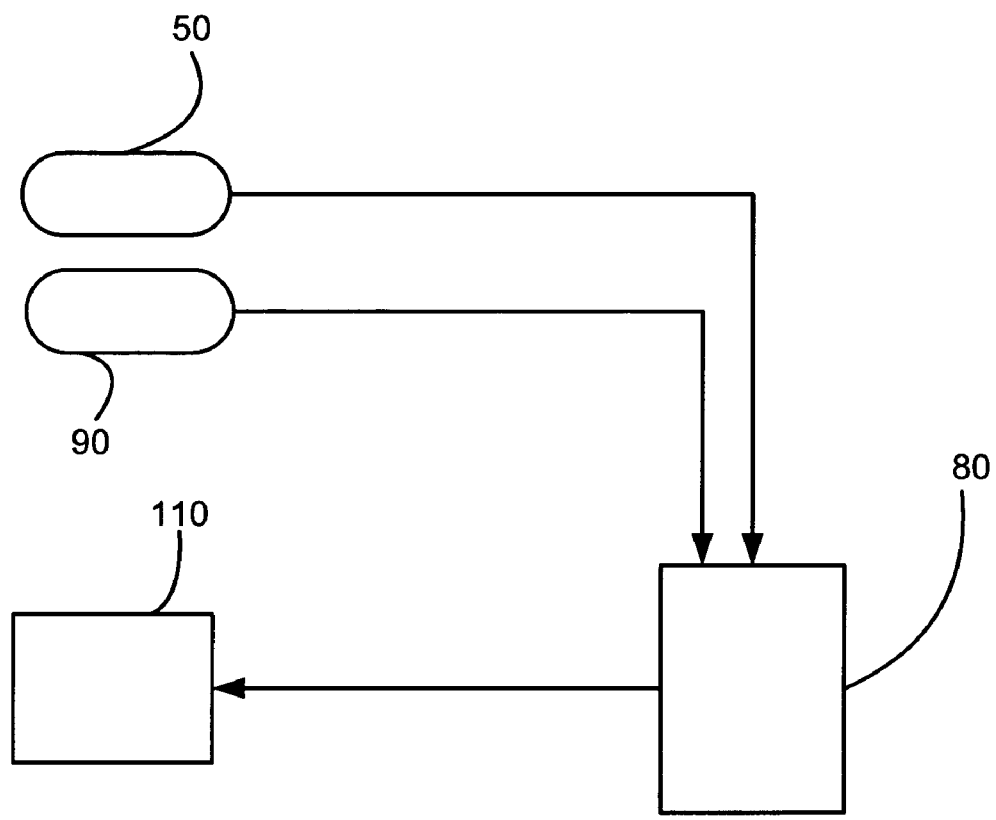
FIG. 4 illustrates another embodiment of a system including a remote device and a single release device.

FIG. 4 illustrates another embodiment of a system for modulating the concentration of a neurotrophin. In this exemplary embodiment of the system, a single release device 110 is used. Release device 110 may be capable of releasing a neurotrophin, an inhibitor of degradation of the neurotrophin, or a composition containing a mixture of neurotrophin and an inhibitor of neurotrophin degradation. Release device 110 and sensors 50 and 90, which are capable of detecting the concentrations of neurotrophin and inhibitor of neurotrophin degradation, respectively, are linked to controller 80. This exemplary system also includes an imaging device 100. Sensors 50 and 90, release device 110, and remote device 100 may be connected to the electronic controller 80 by various methods as described previously. FIG. 4 serves to provide further illustration that the various system components, including sensors, release devices and the remote device, may be combined in various ways. Possible combinations are not limited to the examples presented herein, and systems that use various combinations of system components in various configurations may be appropriate based on a particular embodiment.

Figure 5:
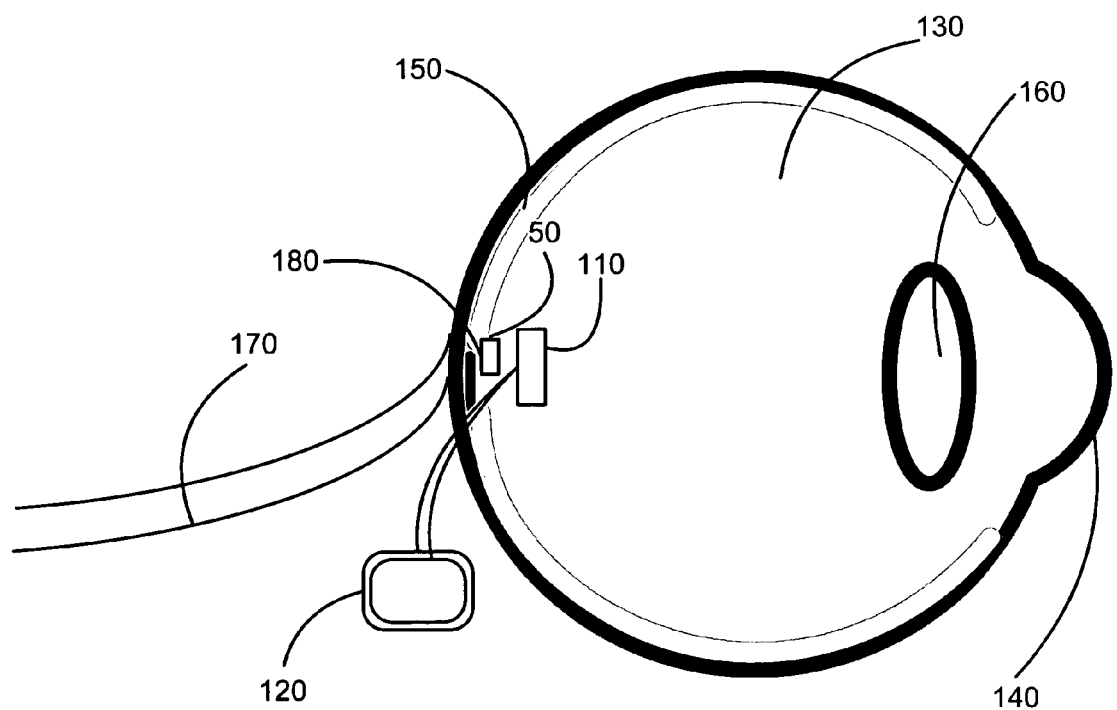
FIG. 5 illustrates an embodiment of a system for implantation within the eye of a subject.
Figure 5:
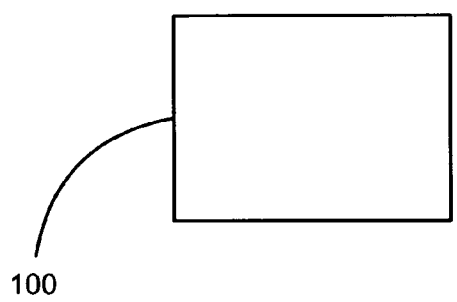

FIG. 5 illustrates in detail a specific exemplary embodiment, which includes implanted structures for delivery of neurotrophin to the eye. Such a system may have application, for example, in the restoration of vision damaged by neural degeneration at the retina such as the types of degeneration seen in aging as well as in diseases such as retinitis pigmentosa and various forms of macular degeneration (see e.g. Adler et al., Mol. Vis. 5:31-36, 2004). Some potential exemplary applications for an embodiment like that diagrammed in FIG. 5 include the treatment of diseases of the optic nerve such as glaucoma, optic neuritis and ischemic optic neuropathy (e.g. Margalit and Sadda, Art. Organs, 27(11):963-974, 2003). Other potential exemplary applications include the treatment of diseases of the retina, such as various types of macular degeneration and diabetic retinopathy (e.g. Green, Mol. Vis. 5:27-36, 1999; Ciulla et al., Diabetes Care 26(9): 2653-2664, 2003). Visual inputs enter eye 130 through cornea 140 and are focused on retina 150 by lens 160. Photodetectors located in the retina may be activated by a visual input to generate neural activity that is carried to the brain via optic nerve 170. Release device 110 releases a neurotrophin in the vicinity of retina 150, while sensor 50 detects the concentration of neurotrophin in the vicinity of the retina 150. Controller 100 is located external to eye 130 and communicates with sensor 50 and release device 110 via wireless connections in this embodiment. Sensor 50 and release device 110 may be placed on the retina at optic disc 180, the region where the optic nerve enters the eye. Since no photoreceptors are found at the optic disc, placement of structures at this location should not interfere with vision.

Neurotrophin and/or neurotrophin degradation inhibitor release devices 60, 70, and 110, as illustrated in the exemplary illustrations of FIGS. 2 through 5, may be any of various types of release devices capable of releasing substances in a controlled fashion responsive to a control signal. The neural support substances may be released in combination with one or more neurotrophins, one or more inhibitors of degradation of a neurotrophin, or both. In some embodiments, suitable devices may include, for example, polymeric components which, when subjected to an applied control such as e.g., electric, magnetic field, change in temperature, change in pH, etc. change in configuration to release a drug or other substance contained by or within the polymer ("Polymers in Controlled Drug Delivery", Brannon-Peppas, Medical Plastics and Biomaterials, November 1997, p. 34). Polymers carriers may be fashioned in a variety of forms, including for example, pellets, discs or capsules (see, e.g., Goodell et al., Am. J. Hosp. Pharm. 43:1454-1461, 1986; Langer et al., "Controlled release of macromolecules from polymers", in Biomedical polymers, Polymeric materials and pharmaceuticals for biomedical use, Goldberg, E. P., Nakagim, A. (eds.) Academic Press, pp. 113-137, 1980; Rhine et al., J. Pharm. Sci. 69:265-270, 1980; Brown et al., J. Pharm. Sci. 72:1181-1185, 1983 and Bawa et al., J. Controlled Release 1:259-267, 1985). Neurotrophins and inhibitors of neurotrophin degradation, and compositions thereof may be linked by occlusion in the matrices of a polymer, bound by covalent linkage, or encapsulated in microcapsules. Within certain embodiments, neurotrophic compositions are provided in non-capsular formulations, such as microspheres (ranging from nanometers to micrometers in size), pastes, films or sprays. Preferably, neurotrophic compositions of the present invention are fashioned in a manner appropriate to the intended use. Within certain aspects of the present invention, the composition should be biocompatible, and release one or more neurotrophin(s) and inhibitor(s) of neurotrophin degradation over a period of several seconds, minutes, hours, days, or months. For example, "quick release" or "burst" compositions are provided that release up to 50% (w/v) of neurotrophins and inhibitors of neurotrophin degradation over a desired period. Such "quick release" compositions should, within certain embodiments, be capable of releasing chemotherapeutic levels (where applicable) of a desired neurotrophin and inhibitor of neurotrophin degradation. In other embodiments, "low release" neurotrophic compositions are provided that release less than 1% (w/v) of a neurotrophin and inhibitor of neurotrophin degradation over a desired period. In certain aspects, neurotrophin and inhibitor of neurotrophin degradation compositions of the present invention should be stable for several months and capable of being produced and maintained under sterile conditions.

Other suitable release devices may include a reservoir of the substance to be released in combination with a controllable pump mechanism for moving the substance out of the reservoir. Such devices are described, for example, in U.S. Pat. Nos. 5,476,446, 5,676,655, 5,713,847, 6,045,528, 6,304, 787, 6,309,410, 6,440,102 and 6,726,678, all of which are incorporated herein by reference in their entirety. A number of designs for microscale (often MEMS-type drug delivery devices) are also known. Examples of such devices are described in U.S. Pat. Nos. 5,797,898, 6,408,878, 6,432,050, 6,454,759, 6,537,256, 6,551,838, 6,668,190, 6,669,683 and 6,673,596, all of which are incorporated herein be reference in their entirety. A good review of methods and system for in vivo drug delivery is provided by "Small-scale systems for in vivo drug delivery", LaVan et al., Nature Biotechnology, Vol. 21, No. 10, October 2003. In some embodiments, the release device is of a type that is not implantable. Examples of such devices may be found in U.S. Pat. Nos. 6,075,066, 6,586,023, 6,756,053, 6,723,077 and 6,684,879, which are incorporated herein by reference. While the above described drug delivery devices are exemplary of devices that may be suitable for use as release devices; the practice of these methods and approaches is not limited to these specific devices. It will be appreciated that depending upon factors such as, but not limited to, the intended target for the released substances, the particular substances to be released, and the intended duration of treatment, that certain delivery devices will be more or less appropriate than others, and that selection of a suitable device may be made by a practitioner of skill in the art, based upon the guidance provided herein. In some embodiments, a plurality of release devices of the same or different types may be used.

Substances released from the release device or devices may include any substances that act to modulate neurotrophin activity in the region near the release device. Such substances include neurotrophins and inhibitors of neurotrophin degradation, and precursors and combinations thereof.

The approaches described herein provide methods for altering levels of neurotrophin (e.g., to enhance nerve growth) by administering an effective amount of neurotrophins and inhibitors of neurotrophin degradation. The neurotrophins and inhibitors of neurotrophin degradation are preferably part of a composition when used in the methods herein. Generally, the compositions comprise one or more compounds of the invention and an appropriate carrier, excipient or diluent, and may range from being suitable or acceptable for environmental uses, to being suitable or acceptable for veterinary uses, to being suitable or acceptable for human use (i.e., pharmaceutically acceptable). Pharmaceutical compositions will include at least one of a pharmaceutically acceptable vehicle, carrier, diluent, or excipient, in addition to one or more neurotrophin and inhibitor of neurotrophin degradation and, optionally, other components. Pharmaceutically acceptable excipients for therapeutic use are well known in the pharmaceutical art, and are described herein and, for example, in Remington's Pharmaceutical Sciences, Mack Publishing Co. (A. R. Gennaro, ed., 18.sup.th Edition, 1990) and in CRC Handbook of Food, Drug, and Cosmetic Excipients, CRC Press LLC (S. C. Smolinski, ed., 1992). The pharmaceutical compositions of the present invention are formulated to allow the compounds contained therein to be bioavailable upon administration of the composition to a subject. The level of neurotrophin at the site of treatment or in circulation after administration can be monitored by various well-established techniques, such as chromatographic or antibody based (e.g., ELISA) assays. See e.g. Hochhaus et al., BMC Pediatrics 1:2, 2001 and Cai et al., J Neurosci., 21(13): 4731-4739 (2001).

Other optional pharmaceutically acceptable excipients are those that may, for example, aid in the administration of the formulation (e.g., anti-irritant, polymer carrier, adjuvant) or aid in protecting the integrity of the components of the formulation (e.g., anti-oxidants and preservatives). The compositions the instant disclosure may be provided in various forms, depending on the amount and number of different pharmaceutically acceptable excipients present. For example, the neurotrophic composition may be in the form of a solid, a semi-solid, a liquid, a lotion, a cream, an ointment, a cement, a paste, a gel, or an aerosol. In certain embodiments, the compositions are in the form of a liquid or gel. The pharmaceutically acceptable excipients suitable for use in the neurotrophic compositions as described herein may include, for example, a viscosity-increasing agent, a buffering agent, a solvent, a humectant, a preservative, a chelating agent, an emollient, an antioxidant, an adjuvant, and the like.

In certain embodiments, compositions of neurotrophins and/or neurotrophin inhibitors in combination with a carrier, diluent, or excipient may also include agents for improving solubility, absorption, stability and other properties, as are known in the art. The released substance or substances may include any agent capable of modulating the activity of the neurotrophin within the region, and may include quantities of neurotrophin, inhibitor of degradation of the neurotrophin or both. The released substance or composition may include precursors or components of neurotrophins which, upon delivery into a neural tissue, are processed to produce a neurotrophin, such that an increase in the concentration of the substance in the tissue produces a corresponding increase in activity of the neurotrophin. For example, an increase in neurotrophin activity may be due to an increase in neurotrophin concentration. The released compositions may include more than one substance that has neurotrophic effects, or may include more than one substance that acts as an inhibitor of degradation of neurotrophin, or may include one or more neural support substances, and any combination thereof.

In some embodiments, the neurotrophin may be a cellular second messenger (also referred to simply as a second messenger), which may be released alone or in combination with the release of another neurotrophin and/or an inhibitor of degradation of the second messenger. As used herein, a "cellular second messenger" may be any chemical, biological agent or compound that mediates cellular activity within the cells of the sensory organ by relaying intracellular signals from an extracellular molecule bound to the cell surface and which creates a resulting neurotrophic effect. The cellular second messenger may be cyclic AMP (cAMP or adenosine 3', 5'-cyclic monophosphate) or one of its biochemical or functional analogs which results in biochemical reactions within a cell similar to those triggered by cAMP. Cellular second messengers may include: forskolin, dibutyric-cAMP (db-cAMP), adenosine 3',5'-cyclic monophosphate benzyl ester (cAMP-Bn), 8-chloroadenosine-3', 5'-cyclic monophosphate (8-Cl-cAMP), 8-(4-Chlorophenylthio)-cAMP (CPT-cAMP), 8-bromo-cAMP (8Br-cAMP), $N^6$, $O^{2'}$-dibutyryl-cAMP ($Bt_2$cAMP), or $N^6,O^{2'}$-dioctanovl-cAMP ($Oco_2$-cAMP). In some cases, a second messenger functional analog may be a substance which is part of the same normal intracellular signaling cascade chain as the second messenger. As will be understood by one skilled in the art, the functional concentration of the second messenger is based on the concentration of the second messenger as well as the concentration of any analogs combined, relative to their respective concentrations and activity kinetics. However, in certain embodiments a second messenger may be released extracellularly to produce an increase in extracellular concentration of the second messenger, following which active or passive transport of the second messenger across the cell membrane may result in an increase in the second messenger concentration within a cell.

As diagrammed in FIGS. 2, 3 and 4, a release device such as 60, 70 may be controlled by a control signal from controller 80. The nature of the control signal will depend upon the particular release device used, and the generation of suitable control signals is known in the relevant art. In some embodiments, a voltage or current control signal may be used. In some embodiments, a voltage or current generated by the controller may be used to generate a magnetic field or provide heating in the situation that direct control of the release device is based on magnetic field or heating. These are merely examples, and other control mechanisms may be suitable for other types of release devices. In some embodiments, the release device may generate a status signal that can be received by the controller. Connection of one or more release devices to the controller for transmission of control and status signals can be via various means known in the art, including by electronic wiring or cabling, or by a wireless connection such as through radio frequency signals. The release device may also include one or more transmitters or receivers as needed to receive control signals and transmit status signals.

The choice of implant site for the release device or devices will depend on the intended neurotrophin target cell(s) or tissue and the particular embodiment. In some cases, a release device (or a portion thereof) may be implanted within a sensory organ (e.g., within the posterior chamber of the eye for access to the retina), or within the scala tympani or scala vestibuli of the cochlea, for access to hair cells. In some cases, a release device will be implanted within or adjacent to the brain or central nervous system. In some cases, the implant location may be near the tissue of interest, such as the olfactory bulbs or the spinal column. In some cases, the release device may include a thin tube or the like that can be threaded into a small space for targeted delivery of a composition, while the remainder of the release device (which might include, for example, a reservoir of the composition) could be implanted in an adjacent region with more available space. The neurotrophin and/or the inhibitor of the degradation of the neurotrophin and/or the neural support substance may be delivered into the interior or to the exterior of a sensory organ, including delivery into a cell or a blood vessel internal to or connected to the sensory organ. In some embodiments, multiple release devices may be used. These may include different release devices for releasing different substances, as illustrated in FIG. 2, or multiple release devices for releasing a single substance. Release devices may be implanted in several different locations in or in the vicinity of the neural tissue or structure that is the target of the treatment.

In some embodiments, the concentration of neurotrophin is monitored and levels are regulated over time through the addition of additional neurotrophin, the addition of inhibitor of degradation of the neurotrophin and/or the addition of neural support substance. In some embodiments, the concentration of neurotrophin may be detected through a sensor or sensor device and the sensor data coupled to the controller. Implantable sensors have been developed for in vivo detection of various analytes, including glucose, proteins, enzymes, metabolites, and toxins. Such sensors frequently are made up of a chemically selective component, which is often biological in nature, in combination with a transducing device. Examples of selective chemical processes include selective absorption into a polymer, selective adsorption or binding to a membrane or coated surface (which may take advantage of specificity of antibodies, enzymes, single strands of DNA, for example), or selective permeability through a biological or bio-based membrane. The selective process of the sensor is typically associated with a change in a property, for example, an optical, mechanical, electrical, or chemical property, that can be detected by the transducing device, which is often a microfabricated MEMS-type device. Examples of sensors suitable for use in various embodiments include those disclosed in U.S. Pat. Nos. 6,201,980, 6,278,379, 6,480,730, 6,673,596, 6,750,311, 6,751,491, 6,754,536, 6,770,179, and RE38525, and U.S. Published Patent Applications Nos. 20030032892, 20030158584, 20030224735, and 20040140209, all of which are incorporated herein by reference in their entirety. The invention is not limited to any particular type of sensors, and the above are merely exemplary. The appropriate choice of sensor will depend on the analyte of interest, intended implantation site, duration of treatment, and other variables which will be identifiable by those of skill in the art.

The sensor or sensors may be of any type or types capable of detecting the concentration of a neurotrophin and/or the inhibitor of degradation in a therapeutically relevant region. Concentrations may be detected directly or indirectly through the detection of biological activity related to the concentration of the substance(s) of interest. The region may be a sensory organ, including those that are auditory, olfactory, visual or somatosensory. The region may be within the peripheral or central nervous system. The choice of sensor(s) used will depend on the specific embodiment, particularly the substance(s) to be detected, the locations and the expected length of time over which the sensor will be needed. In general, sensors that are suitable for continuous use (over at least some generally defined period, e.g. a few days, weeks, or months) are preferred over sensors suitable for one-time use although the selection of one or more sensors will depend on the particular embodiment. In some embodiments, no sensor will be used and the release will occur once or based on a preset delivery schedule. Such embodiments may include those that test patient response. Sensors of different types may be combined in a particular embodiment. Sensors may generate a signal that is a function of the concentration of the detected substance. The signal may be an electrical signal. Certain sensors may generate an electrical signal (current or voltage) directly, while others may generate another type of signal (optical, thermal, pressure, etc.) which may be converted to an electrical signal by suitable transduction means, as are known in the art. Various types of signal generated by the sensor and means by which the signal is transmitted to the controller will be appropriate for different embodiments.

As will be appreciated by one skilled in the art, any detected concentration of the neurotrophin and/or the inhibitor of degradation, as reported by the sensor(s), is inherently an estimate based on the actual concentration of the detected substance at any given time. Moreover, the sensor may be configured to measure concentration of the detected substance at a location that is temporally and/or spatially near, rather than at, the location of interest or the target location. Therefore, while it is presumed that a relationship exists between the measured concentration and the concentration at the target location for delivery, it is not required that the measured concentration be identical to the concentration at the target location for delivery. In some embodiments, multiple sensors may be used. These may include different sensors for detecting different substances, as illustrated in FIG. 2, or multiple sensors for detecting a single substance. In some embodiments and as depicted in FIG. 2, there may be one or more sensors to detect the concentration of neurotrophin as well as one or more sensors to detect the concentration of inhibitor of degradation of the neurotrophin. Sensors may be implanted in several different locations within or in the vicinity of the neural tissue or structure that is the target location for delivery. As with the release devices, sensors may be connected to the controller for transmission of data and possibly control signals via various connection methods known in the art. The connections are not limited to any particular connection method and may be made by electronic or optical wiring or cables, or by a wireless connection such as by radio frequency signals. The sensors may include one or more transmitters or receivers as needed to transmit data signals and, in some embodiments, receive control signals.

Controllers used in various embodiments, as exemplified herein (e.g., controller 80 in FIGS. 2, 3 and 4), may be configured in various ways depending on the embodiment. The controller may be configured to receive signals from sensors and/or release devices, and to send control signals to release devices and/or sensors. The controller may be connected to sensors and release devices by various means known in the art, as described above, and may include one or more transmitters or receivers for transmitting or receiving data, status and control signals as described above. The controller may be placed in various locations. The controller may be external to the body of the mammal, including being located at a distance from the body or capable of being worn on or near the surface of the body. The controller may in addition be connected to remote devices by any connection means known in the art.

One or more parameters may be controlled by the controller. As depicted in FIG. 2, the controller may receive information from one or more sensors (e.g. sensors 50 and 90) regarding concentrations of neurotrophin and/or inhibitor of neurotrophin degradation. In addition the controller may receive information regarding the concentration of one or more neural support substances. The controller may also receive information from one or more sensors regarding one or more biological activities arising from a particular level of neurotrophin and/or inhibitor of degradation of neurotrophin and/or neural support substance. The controller may generate one or more signals that lead to the release of substances from one or more release devices (e.g. release devices 60 and 70). As noted above, the two sensors and two release devices depicted in FIG. 2 are merely exemplary, and the system may include larger or smaller numbers of sensors and release devices. In many cases, the desired end result is to modulate the concentration of neurotrophin within the tissue or cellular structure of interest; however, in many embodiments this may be achieved by elevating one or both of the concentration of neurotrophin and concentration of inhibitor of neurotrophin degradation either within or nearby the tissue or cellular structure of interest.

Other embodiments of the method include regulating the concentration of the neurotrophin and/or the inhibitor of degradation over time and monitoring the levels of the concentration of neurotrophin over time. The concentrations may be kept constant over time, vary in a predetermined manner, be adjusted to keep the concentration within some set parameters and/or be regulated based on the concentration of neurotrophin detected by the sensor.

In some embodiments, the method includes modulating the level of a neurotrophin in a sensory organ of a subject and includes detecting the level of the neurotrophin in the sensory organ, comparing the detected level with a target level of neurotrophin, and if the detected level is less than the target level, releasing an amount of at least one of the neurotrophin and an inhibitor of degradation of the neurotrophin. The target level may be defined as a range of concentrations of the neurotrophin and may vary over time. The target level may be cyclic. The target level of neurotrophin may be based on the concentration of neurotrophin within the sensory organ, in the vicinity of the sensory organ or within a cell of the sensory organ. The rate of release may be controlled based on current and/or target values to provide a gradual ramping up of the release rate and may be controlled by any of the various control methods that are known or may be devised by those of skill in the art such as proportional-integral-derivative (PID) control.

The concentration of neurotrophin(s) in a tissue or cell of interest are modulated by elevating the amounts of neurotrophin and/or inhibitor of neurotrophin degradation and/or neural support substance released into or in the vicinity of the tissue, sensory or neural structure, or cell of interest. In many situations, it may be possible to modulate the level of neurotrophin in several ways such as elevating the concentration of neurotrophin, elevating the concentration of inhibitor of degradation or elevating the concentration of neural support substance or some combination of these in order to achieve the desired target level of neurotrophin. In some situations, it may be desirable to release multiple neurotrophins, multiple inhibitors of degradation of neurotrophin or both. In some cases, the level(s) may be elevated to "biologically effective" levels, which are levels necessary for the intended biological effect on the neuron(s) of interest. For example, the biologically effective level of neurotrophin within a diseased organ may be equivalent to that of a comparable but non-diseased organ, or it may be to a higher level as needed to stimulate neurotrophic effects. In some situations, the level(s) may be elevated one or a few fold while in others the biologically effective level(s) may be several fold higher than before elevation. In some cases, the level(s) may be elevated to "therapeutically effective" levels, which are levels necessary to achieve a desired therapeutic effect. For example, in a situation where the therapeutic effect desired or intended is regeneration of a neuron, the therapeutically effective levels are those in a range that may be expected to stimulate regeneration. In some cases, the level(s) may be increased to "normal" levels, which are levels in the range of those found or predicted to be found in the same anatomic location in healthy individuals. In some cases, the level(s) are increased from one or more "baseline" levels, which are levels detected prior to start of treatment or detected during a time interval between compound release(s). Depending on the intended effect, the levels may be increased to or toward normal levels (in cases where the initial level was below normal) or increased to higher-than normal levels. The target level may be a predetermined constant value (which might be, for example, a value that represents a desirable normal or supra-normal value). The target level may be calculated as a percentage or multiple of the initial concentration value. The target level may have a marked time-dependence and be cyclic, including having multiple target levels over multiple time points. In some embodiments, a time-dependent series of target values may be stored or calculated. Such values may be predetermined values stored in one or more memory devices. For example, in certain embodiments the target level may initially be a higher than normal value, in order to promote repair or recovery following a period of sub-normal concentrations, and then after a period of time, the target value may be lowered to a normal level. Various schemes may be devised for determining a target value as a function of the current and an eventual target value.

As an example, in some embodiments, the controller may adjust the amount of the substance(s) of interest (e.g., neurotrophin, inhibitor of neurotrophin degradation, or neural support substance) delivered by the system such that the concentration of the neurotrophin, the concentration of the inhibitor of degradation, or both may be increased by up to about 50% over preexisting levels. In other embodiments, the concentration of the substance(s) of interest may be increased by about two-fold to 100-fold over the preexisting levels. In still other embodiments, the concentration of the substance(s) of interest may be elevated to a biologically or therapeutically effective level. The concentration of the substance(s) of interest may also be increased to level(s) that are detectable by the sensors or other means.

In some embodiments, some of the neurotrophin and/or the inhibitor of degradation of the neurotrophin and/or the neural support substance may be produced by the mammal itself while in others the neurotrophin and/or the inhibitor of degradation of the neurotrophin and/or the neural support substance may be entirely supplied by the method, and models that take into account the influence of endogenous and exogenous sources may be included in the control scheme. In some embodiments, the neurotrophin and/or the inhibitor of degradation of the neurotrophin are introduced as precursors and endogenous factors alter the precursor(s) to metabolically active forms after release. The methods and systems described herein, therefore, include precursors, metabolites and other functionally equivalent substances to the neurotrophins, inhibitors of degradation of neurotrophin and neural support substances described.

Electrical circuitry, such as processor 120 (presented in the controller 100 of FIG. 3) may control the release of neurotrophin, inhibitor of degradation, neural support substance or some combination of these in order to modulate the concentration of neurotrophin toward a target level. The concentration of neurotrophin is determined based on signals from detectors 50 and 90 in the embodiment diagrammed in FIG. 2, for example. Based on current levels of neurotrophin and inhibitor, the processor produces a control signal to drive the release device(s) to release the composition(s) in order to modulate the levels to target levels in the exemplary embodiment shown in FIG. 2. The rate of release of the composition may occur over a predetermined time period to provide a controlled rate of release of the composition. The target concentration of the composition may be constant over time, it may vary as a function of time over a predetermined time period, it may comprise a predetermined sequence of target values, it may be calculated as a function of the detected concentration, or at different time periods the target concentration may be determined by any of the aforementioned calculations.

The processor 120 or another portion of the system may include a memory device capable of storing a target set of levels of neurotrophin or other parameters such as, for example, times and amounts of substance(s) to be released. In some embodiments, the method includes detecting the concentration of the neurotrophin in a therapeutically relevant region of the nervous system of a subject, calculating a quantity of a composition to be released in the region and releasing the calculated quantity in the region. The detection and/or release may happen at one or more times in one or more locations. The calculated quantity may be any quantity of the composition that is sufficient to adjust the detected concentration of neurotrophin toward a target concentration. The detection and release may be repeated over time in order to obtain and maintain a desired concentration of neurotrophin in the region.

The processor 120 may be of a number of types that are capable of comparing a directly or indirectly detected concentration of the neurotrophin with a target level in order to compute a quantity of a composition to be released to adjust the detected concentration toward a target concentration. Various combinations of hardware, firmware, software, analog and/or digital circuitry may be used in the controller. The controller may be implanted at or near the site of the sensors or release devices, or it may be located at a distance from these devices and connected via a wireless link, as described above. In some embodiments, the processor is worn externally relative to the skin surface of the subject. The control signal generator may be of any type that is capable of generating a control signal representing a computed quantity of the composition to be released. The computed quantity of the composition may be intended to be released over a fixed time period so that the controlled release device controls a rate of release of the composition.

In some aspects, the system that modulates the concentration of a neurotrophin may include a sensor, a feedback signal generator, a transmitter, a receiver and/or a controlled release device such as the sensors 50, 90 of FIG. 2. In some embodiments, the sensor is capable of detecting the concentration of the neurotrophin in the vicinity of a highly innervated tissue of a mammal. The feedback signal generator may be capable of representing the detected concentration of neurotrophin in a feedback signal. The transmitter may be adapted for transmitting the feedback signal to a remote processor. In some embodiments, the receiver is adapted for receiving a control signal from said remote processor. The controlled release device may be implanted in the vicinity of a highly innervated tissue and controllable by the control signal to release a composition capable of modulating the concentration of the neurotrophin in the vicinity of the highly innervated tissue.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs.

Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical or biological aspects of implementations will require optically-oriented or biologically-oriented hardware, software, and or firmware.

One exemplary application for the methods and systems described herein is to restore the sensory hair cells within the cochlea which lead to hearing loss when damaged. A common cause of acquired hearing loss is damage to the sensory hair cells within the cochlea, which can arise due to excessive exposure to loud noise, infection and/or ototoxic drugs. See Wang et al., J Neurosci., 23(24):8596-8607 (2003). Under normal metabolic conditions, damage to hair cells limits their function and therefore the ability of the individual to hear is reduced. See Kawamoto et al., J Neurosci., 23(11): 4395-4400, 2003. An implantable release device or devices as described herein could be implanted within the cochlea or in a therapeutically effective region to the cochlea in a person or animal that has hair cell damage. The release device(s) could then be used to increase the metabolic levels of neurotrophin in the region of the hair cells, initiating and promoting the growth of replacement hair cells and/or repairing and maintaining those that exist as described herein. For background, see the 36th Karolinska Institutet Nobel Conference: *To Restore Hearing,* 9-13 Jun. 2002, Krusenberg, Sweden. In certain embodiments, the neurotrophin modulating substance(s) or compositions described herein could be released in conjunction with ototoxic drugs to prevent hearing loss as a negative side effect of the drug therapy. In other embodiments, the substance(s) or compositions described herein could be released to repair previous damage. For example, the release could include ongoing release, release at periodic intervals, or only one or a limited number of releases to retain and repair hearing.

The foregoing detailed description has set forth various embodiments of the devices and/or processes via the use of block diagrams, flow charts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that some of the mechanisms of the subject matter described herein are capable of being distributed as a program product in a variety of forms, and that an illustrative embodiment of the subject matter described herein applies equally regardless of the particular type of signal-bearing media used to actually carry out the distribution. Examples of signal-bearing media such as may be used to store programs and data include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

As used herein, the term "about" or "consists essentially of" refers to ±15% of any indicated structure, value, or range. Any numerical ranges recited herein (e.g., concentrations, ratios, percentages, sequences, etc.) are to be understood to include any integer within that range and, where applicable, fractions thereof, such as one tenth and one hundredth of an integer (unless otherwise indicated).

The above referenced technical articles are specifically incorporated herein by reference in their entirety for all that they disclose and teach. In an event of any conflict between the instant application and a referenced technical article, the instant application controls.

Although the methods, devices, systems and approaches herein have been described with reference to certain preferred embodiments, various modifications may be made without deviating from the spirit and scope of the invention. As illustrated by the foregoing examples, various choices of sensor and release device configuration may be within the scope of the invention. As has been discussed, the choice of system configuration may depend on the intended application of the system, the environment in which the system is used, cost, personal preference or other factors. Signal analysis and release device control processes may be modified to take into account choices of sensor, release device, and implant site, released and detected substances, and system configuration, and such modifications, as known to those of skill in the relevant arts, may fall within the scope of the invention. Therefore, the full spirit or scope of the invention is defined by the appended claims and their legal equivalent and is not be limited to the specific embodiments described herein.

What is claimed is:

1. A method of elevating, in a highly innervated tissue in a subject, the concentrations of at least one neurotrophin and at least one inhibitor of degradation of said neurotrophin, comprising:
   (a) introducing into a highly innervated tissue in a subject at least one neurotrophin to elevate a neurotrophin concentration of the at least one neurotrophin within the highly innervated tissue;
   (b) introducing into the highly innervated tissue at least one inhibitor of degradation of the at least one neurotrophin to elevate an inhibitor concentration of the at least one inhibitor of degradation of said neurotrophin within the highly innervated tissue; and
   (c) regulating the concentration of the neurotrophin over time, wherein regulating includes:
   monitoring, with at least one implanted sensor device, the neurotrophin concentration to determine whether at least one desired neurotrophin concentration target level of the at least one neurotrophin is present; and
   adding additional neurotrophin in a quantity sufficient to adjust the neurotrophin concentration toward the at least one desired neurotrophin concentration target level.

2. The method as in claim 1, wherein the subject is a human.

3. The method as in claim 1, wherein the highly innervated tissue is present in a central nervous system.

4. The method as in claim 1, wherein the highly innervated tissue is present in a peripheral nervous system.

5. The method as in claim 1, wherein monitoring the at least one neurotrophin concentration includes:
   monitoring the neurotrophin concentration within the innervated tissue.

6. The method as in claim 1, wherein the at least one neurotrophin includes adenosine 3', 5'-cyclic monophosphate (cAMP).

7. The method as in claim 1, wherein the step of introducing at least one neurotrophin includes releasing the at least one neurotrophin from a release device.

8. The method as in claim 7 wherein the release device includes a plurality of release devices.

9. The method as in claim 1, wherein the at least one neurotrophin is selected from the group consisting of: nerve growth factor (NGF), brain-derived neurotrophic factor (BDNF), neurotrophin-3 (NT-3), neurotrophin-4 (NT-4), neurotrophin-6 (NT-6), and neurotrophin-7 (NT-7).

10. The method as in claim 1, wherein the at least one neurotrophin is selected from the group consisting of: nerve growth factor (NGF), brain-derived neurotrophic factor (BDNF), neurotrophin-3 (NT-3), neurotrophin 4/5 (NT-4/5), ciliary neurotrophic factor (CNTF), leukemia inhibitory factor/cholinergic differentiation factor (LIF/CDF), cardiotrophin-1, basic fibroblast growth factor (bFGF), acidic fibroblast growth factor (aFGF), fibroblast growth factor-5 (FGF-5), insulin, insulin-like growth factor I (IGF-I), insulin-like growth factor II (IGF-II), transforming growth factor $\beta 1$ (TGF $\beta 1$), transforming growth factor $\beta 2$ (TGF $\beta 2$), transforming growth factor $\beta 3$ (TGF $\beta 3$), activin, glial cell-derived neurotrophic factor (GDNF), midkine, heparin-binding neurotrophic factor (HBNF), pleiotrophin, epidermal growth factor (EGF), transforming growth factor $\alpha$ (TGF $\alpha$), schwannoma-derived growth factor, heregulin (neuroregulin, ARIA), interleukin 1, interleukin 2, interleukin 3, interleukin 6, axon ligand-1 (Al-1), elf-1, ehk1-L, and LERK2.

11. The method as in claim 1, wherein the at least one neurotrophin includes a cellular second messenger.

12. The method as in claim 1, wherein the at least one neurotrophin is selected from the group consisting of: forskolin, dibutyric-cAMP (db-cAMP), adenosine 3', 5'-cyclic monophosphate benzyl ester (cAMP-Bn), 8-chloroadenosine-3',5'-cyclic monophosphate (8-Cl-cAMP), 8-(4-Chlorophenylthio)-cAMP(CPT-cAMP), 8-bromo-cAMP (8Br-cAMP), $N^6,O^{2'}$-dibutyryl-cAMP ($Bt_2$cAMP), and $N^6,O^{2'}$-dioctanoyl-cAMP ($O_{CO2}$-cAMP).

13. The method as in claim 1, wherein the at least one neurotrophin is elevated extracellularly within the highly innervated tissue.

14. The method as in claim 1, wherein the at least one neurotrophin is elevated intracellularly within the highly innervated tissue.

15. The method as in claim 1, wherein the at least one inhibitor of degradation includes erythro-9-(2-hydroxy-3-nonyl)adenine.

16. The method as in claim 1, wherein the at least one inhibitor of degradation is selected from the group consisting of: milrinone, aminone, pimobendan, and enoximone.

17. The method as in claim 1, wherein the at least one inhibitor of degradation is selected from the group consisting of: rolipram, Ro 20-1724, denbufylline, RS 25344, CP80633, SB207499, RP 73401, CDP 840, and zadarverine.

18. The method as in claim 1, wherein the at least one inhibitor of degradation includes zaprinast.

19. The method as in claim 1, wherein the at least one inhibitor of degradation includes dipyridimole.

20. The method as in claim 1, wherein the desired target level of the at least one neurotrophin is a therapeutically effective level.

21. The method as in claim 1, wherein the desired target level of the at least one neurotrophin is a normal level.

22. The method as in claim 1, wherein the desired target level of the at least one neurotrophin is a baseline level.

23. A method of elevating, in a highly innervated tissue in a subject, the concentrations of at least one neurotrophin and at least one inhibitor of degradation of said neurotrophin, comprising:
   (a) introducing into a highly innervated tissue in a subject at least one neurotrophin to elevate a neurotrophin concentration of the at least one neurotrophin within the highly innervated tissue;
   (b) introducing into the highly innervated tissue at least one inhibitor of degradation of the at least one neurotrophin to elevate an inhibitor concentration of the at least one inhibitor of degradation of said neurotrophin within the highly innervated tissue; and
   (c) regulating the concentration of said at least one inhibitor of degradation of the neurotrophin over time, wherein regulating includes:
   monitoring, with at least one implanted sensor device, the inhibitor concentration to determine whether at least one desired inhibitor concentration target level of the at least one inhibitor of degradation is present; and
   adding additional inhibitor of degradation in a quantity sufficient to adjust the inhibitor concentration toward the at least one desired inhibitor concentration target level.

24. The method as in claim 23, wherein the subject is a human.

25. The method as in claim 23, wherein the highly innervated tissue is present in a central nervous system.

26. The method as in claim 23, wherein the highly innervated tissue is present in a peripheral nervous system.

27. The method as in claim 23, wherein monitoring the at least one inhibitor of degradation concentration includes:
monitoring the inhibitor concentration within the innervated tissue.

28. The method as in claim 23, wherein the at least one neurotrophin includes adenosine 3', 5'-cyclic monophosphate (cAMP).

29. The method as in claim 23, wherein the step of introducing at least one inhibitor of degradation includes releasing the at least one inhibitor of degradation from a release device.

30. The method as in claim 29 wherein the release device includes a plurality of release devices.

31. The method as in claim 23, wherein the at least one neurotrophin is selected from the group consisting of: nerve growth factor (NGF), brain-derived neurotrophic factor (BDNF), neurotrophin-3 (NT-3), neurotrophin-4 (NT-4), neurotrophin-6 (NT-6), and neurotrophin-7 (NT-7).

32. The method as in claim 23, wherein the at least one neurotrophin is selected from the group consisting of: nerve growth factor (NGF), brain-derived neurotrophic factor (BDNF), neurotrophin-3 (NT-3), neurotrophin 4/5 (NT-4/5), ciliary neurotrophic factor (CNTF), leukemia inhibitory factor/cholinergic differentiation factor (LIF/CDF), cardiotrophin-1, basic fibroblast growth factor (bFGF), acidic fibroblast growth factor (aFGF), fibroblast growth factor-5 (FGF-5), insulin, insulin-like growth factor I (IGF-I), insulin-like growth factor II (IGF-II), transforming growth factor β1 (TGF β1), transforming growth factor β2 (TGF β2), transforming growth factor β3 (TGF β3), activin, glial cell-derived neurotrophic factor (GDNF), midkine, heparin-binding neurotrophic factor (HBNF), pleiotrophin, epidermal growth factor (EGF), transforming growth factor α (TGF α), schwannoma-derived growth factor, heregulin (neuroregulin, ARIA), interleukin 1, interleukin 2, interleukin 3, interleukin 6, axon ligand-1 (Al-1), elf-1, ehk1-L, and LERK2.

33. The method as in claim 23, wherein the at least one neurotrophin includes a cellular second messenger.

34. The method as in claim 23, wherein the at least one neurotrophin is selected from the group consisting of: forskolin, dibutyric-cAMP (db-cAMP), adenosine 3', 5'-cyclic monophosphate benzyl ester (cAMP-Bn), 8-chloroadenosine-3',5'-cyclic monophosphate (8-Cl-cAMP), 8-(4-Chlorophenylthio)-cAMP(CPT-cAMP), 8-bromo-cAMP (8Br-cAMP), $N^6,O^2$-dibutyryl-cAMP ($Bt_2$cAMP), and $N^6,O^2$-dioctanoyl-cAMP ($O_{CO2}$-cAMP).

35. The method as in claim 23, wherein the at least one inhibitor of degradation includes erythro-9-(2-hydroxy-3-nonyl)adenine.

36. The method as in claim 23, wherein the at least one inhibitor of degradation is selected from the group consisting of: milrinone, aminone, pimobendan, and enoximone.

37. The method as in claim 23, wherein the at least one inhibitor of degradation is selected from the group consisting of: rolipram, Ro 20-1724, denbufylline, RS 25344, CP80633, SB207499, RP 73401, CDP 840, and zadarverine.

38. The method as in claim 23, wherein the at least one inhibitor of degradation includes zaprinast.

39. The method as in claim 23, wherein at the at least one inhibitor of degradation includes dipyridimole.

40. The method as in claim 23, wherein the desired target level of the at least one inhibitor of degradation is a therapeutically effective level.

41. The method as in claim 23, wherein the desired target level of the at least one inhibitor of degradation is a normal level.

42. The method as in claim 23, wherein the desired target level of the at least one inhibitor of degradation is a baseline level.

43. A method of elevating, in a highly innervated tissue in a subject, the concentrations of at least one neurotrophin and at least one inhibitor of degradation of said neurotrophin, comprising:
(a) introducing into a highly innervated tissue in a subject at least one neurotrophin to elevate a neurotrophin concentration of the at least one neurotrophin within the highly innervated tissue;
(b) introducing into the highly innervated tissue at least one inhibitor of degradation of the at least one neurotrophin to elevate an inhibitor concentration of the at least one inhibitor of degradation of said neurotrophin within the highly innervated tissue; and
(c) regulating the concentration of said at least one inhibitor of degradation of the neurotrophin over time, wherein regulating includes:
monitoring the inhibitor concentration to determine whether at least one desired inhibitor concentration target level of the at least one inhibitor of degradation is present; and
adding additional inhibitor of degradation in a quantity sufficient to adjust the inhibitor concentration toward the at least one desired inhibitor concentration target level; and
(d) regulating the concentration of the neurotrophin over time, wherein regulating includes:
monitoring, with at least one implanted sensor device, the neurotrophin concentration to determine whether at least one desired neurotrophin concentration target level of the at least one neurotrophin is present; and
adding additional neurotrophin in a quantity sufficient to adjust the neurotrophin concentration toward the at least one desired neurotrophin concentration target level.

* * * * *

UNITED STATES PATENT AND TRADEMARK OFFICE
CERTIFICATE OF CORRECTION

PATENT NO. : 8,309,057 B2
APPLICATION NO. : 11/150861
DATED : November 13, 2012
INVENTOR(S) : Ishikawa et al.

It is certified that error appears in the above-identified patent and that said Letters Patent is hereby corrected as shown below:

Column 22
Line 25, change "aminone" to --amrinone--

Column 23
Line 52, change "aminone" to --amrinone--

Signed and Sealed this
Twenty-sixth Day of February, 2013

Teresa Stanek Rea
*Acting Director of the United States Patent and Trademark Office*